US007893215B2

(12) United States Patent (10) Patent No.: US 7,893,215 B2
Bowman et al. (45) Date of Patent: Feb. 22, 2011

(54) AGONIST ANTIBODIES TO IL-23 RECEPTOR

(75) Inventors: Edward P. Bowman, San Carlos, CA (US); Shi-Juan Chen, San Ramon, CA (US); Daniel J. Cua, Boulder Creek, CA (US); Kevin W. Moore, Palo Alto, CA (US); Tatyana Churakova, Sunnyvale, CA (US); Hong-Nhung Y. Nguyen, Santa Clara, CA (US); Jason R. Chan, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/507,642

(22) Filed: Jul. 22, 2009

(65) Prior Publication Data

US 2009/0285777 A1 Nov. 19, 2009

Related U.S. Application Data

(60) Division of application No. 12/026,437, filed on Feb. 5, 2008, now Pat. No. 7,575,741, which is a continuation of application No. 10/742,405, filed on Dec. 18, 2003, now Pat. No. 7,332,156.

(60) Provisional application No. 60/436,274, filed on Dec. 23, 2002.

(51) Int. Cl.
*C07K 16/28* (2006.01)
(52) U.S. Cl. ............ 530/387.1; 530/388.1; 530/388.15; 530/388.22
(58) Field of Classification Search ........................ None
See application file for complete search history.

(56) References Cited

U.S. PATENT DOCUMENTS

| 5,530,101 | A | * | 6/1996 | Queen et al. ............. 530/387.3 |
| 6,001,357 | A | | 12/1999 | Wong et al. |
| 7,332,156 | B2 | | 2/2008 | Bowman et al. |

FOREIGN PATENT DOCUMENTS

| WO | WO 01/18051 A | 3/2001 |
| WO | WO 01/85790 A | 11/2001 |

OTHER PUBLICATIONS

Parham et al (2002), J. Immunol. vol. 168, pp. 5699-5708.*
Chuntharapai et al (1997), Methods in Enzymol. vol. 288, pp. 15-27.*
Kohler and Milstein (1975), Nature, vol. 256, pp. 495-497.*
Aggarwal, Sudeepta, and Gurney, Austin L., "IL-17: prototype member of an emerging cytokine family", *J. Leukoc. Biol.* 71:1-8; 2002.
Benson, J., et al. (Mar. 22, 2002) *FASEB Journal* 16(5):A1045 abstract, "The role of IL-23 in experimental autoimmune encephalomyelitis".
Bonifaz, Laura, et al., "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", *J. Exp. Med.*, 196(12):1627-1638, Dec. 16, 2002.
Brok, et al., "Prevention of experimental autoimmune encephalomyelitis in common marmosets using an anti-IL-12p40 monoclonal antibody," *Journal of Immunology* (Dec. 1, 2002) 169:6554-6563.
Calhoun, Jason H., et al., "Diabetic Foot Ulcers and Infections: Current Concepts", *Advances in Skin & Wound Care*, pp. 31-45, Jan./Feb. 2002.
Cohen, I. Kelman, and Mast, Bruce A., "Models of Wound Healing", *The Journal of Trauma*, 30(12 Supp.):S149-155, Dec. 1990.
Cooper, Andrea M., et al., "Mice Lacking Bioactive IL-12 Can Generate Protective, Antigen-Specific Cellular Responses to Mycobacterial Infection Only if the IL-12 p40 Subunit Is Present", *The Journal of Immunology*, 168:1322-1327, 2002.
Cordoba-Rodriguez, et al., "IL-23 and IL-27: new members of the growing family of IL-12 related cytokines with important implications for therapeutics," *Expert Opinion on Biological Therapy* (Aug. 2003) 3(5):715-723.
Costa, et al., "Adoptive immunotherapy of experimental autoimmune encephalomyelitis via T cell delivery of the IL-12 p40 subunit," *Journal of Immunology* (Aug. 15, 2001) 167(4):2379-2387.
Da Costa, Ricardo Marques, et al., "Double-blind Randomized Placebo-controlled Trial of the Use of Granulocyte-Macrophage Colony-stimulating Factor in Chronic Leg Ulcers", *Am. J. Surg.*, 173:165-168, 1997.
Edde, Lynn, et al., "Lactoferrin protects neonatal rats from gut-related systemic infection", *Am. J. Physiol. Gastrointest Liver Physiol.*, 281:G1140-G1150, 2001.
Elkins, Karen L., et al., "In Vivo Clearance of an Intracellular Bacterium, *Francisella tularensis* LVS, Is Dependent on the p40 Subunit of Interleukin-12 (IL-12) but Not on IL-12 p70", *Infection and Immunity*, 70(4):1936-1948, Apr. 2002.
Engelhardt, Eva, et al., "Chemokines IL-8, GROα, MCP-1, IP-10, and Mig Are Sequentially and Differentially Expressed During Phase-Specific Infiltration of Leukocyte Subsets in Human Wound Healing", *American Journal of Pathology*, 153(6):1849-1860, Dec. 1998.
Gallucci, Randle M., et al., "Interleukin-6 Treatment Augments Cutaneous Wound Healing in Immunosuppressed Mice", *Journal of Interferon and Cytokine Research*, 21:603-609, 2001.
Gillitzer, Reinard, and Goebeler, Matthias, "Chemokines in cutaneous wound healing", Journal of Leukocyte Biology, 69:513-521, Apr. 2001.
Gottrup, Finn, et al., "Models for use in wound healing research: A survey focusing on in vitro and in vivo adult soft tissue", *Wound Repair and Regeneration*, 8(2):83-96, 2000.
Grellner, Wolfgang, "Time-dependent immunohistochemical detection of proinflammatory cytokines (IL-1β, IL-6, TNF-α) in human skin wounds", *Forensic Science International*, 130:90-96, 2002.
Hölscher, Christoph, et al., "A Protective and Agonistic Function of IL-12p40 in Mycobacterial Infection", *The Journal of Immunology*, 167:6957-6966, 2001.

(Continued)

*Primary Examiner*—Prema Mertz
(74) *Attorney, Agent, or Firm*—Gregory R. Bellomy

(57) ABSTRACT

Provided are methods of treatment for skin disorders. In particular, treatment, the skin disorders are generally inflammatory skin disorders, including improper wound healing. Provided are methods of using of a cytokine molecule.

8 Claims, No Drawings

OTHER PUBLICATIONS

Khavari, P.A., et al., "Cutaneous gene transfer for skin and systemic diseases", *Journal of Internal Medicine*, 252:1-10, 2002.

Kraft, William G., et al., "Cutaneous Infection in Normal and Immunocompromised Mice", *Infection and Immunity*, 52(3):707-713, Jun. 1986.

Lehmann, Jörg, et al., "IL-12p40-Dependent Agonistic Effects on the Development of Protective Innate and Adaptive Immunity Against *Salmonella* Enteritidis", *The Journal of Immunology*, 167:5304-5315, 2001.

Liu, Wei, et al., "Gene Therapy of Scarring: A Lesson Learned from Fetal Scarless Wound Healing", *Yonsei Medical Journal*, 42(6):634-645, 2001.

Maeyama, et al., "Attenuation of Bleomycin-induced pneumopathy in mice by monoclonal antibody to interleukin-12," *American Journal of Physiology, Lung Cellular and Molecular Physiology* (Jun. 2001) 280(6):L1128-L1137.

Mikayama et al. (1993) *Proc. Nat'l Acad. Sci.* (USA) 90:10056 "Molecular cloning and functional expression of a cDNA encoding glycosylation-inhibiting factor".

Moulin, Véronique, et al., "Modulated Response to Cytokines of Human Wound Healing Myofibroblasts Compared to Dermal Fibroblasts", *Experimental Cell Research*, 238:283-293, 1998.

Oppmann, Birgit, et al., "Novel p19 Protein Engages IL-12p40 to Form a Cytokine, IL-23, with Biological Activities Similar as Well as District from IL-12", *Immunity*, 13:715-725, Nov. 2000.

Padigel, Udaikumar M., et al., "The Development of a Th1-Type Response and Resistance to *Leishmania major* Infection in the Absence of CD40-CD40L Costimulation", *The Journal of Immunology*, 167:5874-5879, 2001.

Parham, Christi, et al., "A Receptor for the Heterodimeric Cytokine IL-23 Is Composed of IL-12Rβ1 and a Novel Cytokine Receptor Subunit, IL-23R", *The Journal of Immunology*, 168:5699-5708, 2002.

Parks, William C., et al., "Matrilysin in Epithelial Repair and Defense", *Chest*, 120(1):36S-41S, Jul. 2001 Supplement.

Payne, Wyatt G., et al, "Long-term outcome study of growth factor-treated pressure ulcers", *The American Journal of Surgery*, 181:81-86, 2001.

Presky, et al. (1995) *Res. Immunol.* 146:439-445. "IL12 receptors and receptor antagonists".

Schwentker, Ann, et al, "Nitric oxide and wound repair: role of cytokines?", *Nitric Oxide*, 7:1-10, 2002.

Singer, Adam J., and Clark, Richard A.F., "Cutaneous Wound Healing", *The New England Journal of Medicine*, 341(10):738-746, Sep. 2, 1999.

Schaffer, Christopher J., and Nanney, Lillian B., "Cell Biology of Wound Healing", *International Review of Cytology*, 169:151-181, 1996.

Sugawara, Tadaki, et al., "Regulation and Role of Interleukin 6 in Wounded Human Epithelial Keratinocytes", *Cytokine*, 15(6):328-336, Sep. 21, 2001.

Sullivan, Tory P, et al., "The pig as a model for human wound healing", *Wound Repair and Regeneration*, 9(2):66-76, Mar.-Apr. 2001.

Supplementary Partial European Search Report dated May 18, 2007 in counterpart European Patent Application No. 03814312.9.

Voet et al. (1990) *Biochemistry*, at pp. 126-128 and 228-234.

Walter, Michael J., et al., "Interleukin 12 p40 Production by Barrier Epithelial Cells during Airway Inflammation", *Journal of Experimental Medicine*, 193(3):339-351, Feb. 5, 2001.

Werner, S. and Grose, R., "Regulation of Wound Healing by Growth Factors and Cytokines", *Physiol. Rev.*, 83:835-870, 2003.

Wiekowski, Maria T., et al., "Ubiquitous Transgenic Expression of the IL-23 Subunit p19 Induces Multiorgan Inflammation, Runting, Infertility, and Premature Death", *The Journal of Immunology*, 166:7563-7570, 2001.

Wilson, Carole L., et al., "Regulation of Intestinal α-Defensin Activation by the Metalloproteinase Matrilysin in Innate Host Defense", *Science*, 286:113-117, Oct. 1, 1999.

\* cited by examiner

US 7,893,215 B2

AGONIST ANTIBODIES TO IL-23 RECEPTOR

This application is a Divisional patent application of U.S. patent application Ser. No. 12/026,437, filed Feb. 5, 2008, now U.S. Pat. No. 7,575,741, issued Aug. 18, 2009, which is a Continuation of U.S. patent application Ser. No. 10/742,405, filed Dec. 18, 2003, now U.S. Pat. No. 7,332,156, issued on Feb. 19, 2008, which claims benefit of U.S. Provisional Patent Application No. 60/436,274, filed Dec. 23, 2002, each of which is incorporated herein by reference.

The Sequence Listing filed electronically herewith is also hereby incorporated by reference in its entirety (File Name: DX01578KQB_SeqListing.txt; Date Created: Jul. 22, 2009; File Size: 44.0 KB.)

FIELD OF THE INVENTION

The present invention relates generally to uses of mammalian cytokine-like molecules and related reagents. More specifically, the invention relates to identification of mammalian cytokine-like proteins and inhibitors thereof that modulate skin or wound healing, e.g., inflammatory skin conditions.

BACKGROUND OF THE INVENTION

Cytokines are small proteins that mediate signaling and communication between cells of the immune system, e.g., T cells, B cells, dendritic cells, and macrophages. These proteins mediate a number of cellular activities, including proliferation, growth, differentiation, migration, cell activation, and response to infection, foreign antigens, and wounds.

A particularly important family of cytokines is interleukin-6 (IL-6) family. These cytokines exhibit a wide range of often overlapping biological functions that are transmitted via multichain cell surface receptors, which are typically formed by high-affinity, cytokine-specific receptor chains and lower-affinity, signal-transducing chains. Receptor subunits are often shared among members of this cytokine subfamily.

Recently, a novel helical cytokine was identified that has structural homology to the IL-6 family of cytokines. This protein was designated p19, and was shown to be part of a novel composite factor consisting of a disulfide-bridged complex between p19 and the p40 subunit of IL-12. This novel p19p40 complex, also known as IL-23, is naturally expressed by activated mouse and human dendritic cells and has biological activities that are similar to but distinct from IL-12 (see, e.g., Oppmann et al. (2000) *Immunity* 13:715-725). The p19 subunit of IL-23 is also known as "IL-23p19."

The present invention identifies and provides IL-23, IL-23 agonists, and variants and derivatives thereof, as modulators of skin disorders, for example, for use in the treatment or diagnosis of skin conditions and disorders or wound healing, see, e.g., Fitzpatrick, et al. (eds.) (1993) *Dermatology in General Medicine* 4th ed., McGraw-Hill, N.Y.; Bos (ed.) (1989) *Skin Immune System*, CRC Press, Boca Raton, Fla.; Callen (1996) *General Practice Dermatology*, Appleton and Lange, Norwalk, Conn.; Rook, et al. (eds.) (1998) *Textbook of Dermatology*, Blackwell Publ., Malden, Mass.; Habifor and Habie (1995) *Clinical Dermatology: A Color Guide to Diagnosis and Therapy*, Mosby, Phila., Pa.; Grob (ed.) (1997) *Epidemiology, Causes and Prevention of Skin Diseases*, Blackwell, Malden, Mass.; Hess and Salcido (2000) *Wound Care*, Springhouse Pub. Co., Springhouse, Pa.; Mani, et al. (1999) *Chronic Wound Healing: Clinical Measurement and Basic*, Balliere Tindall Ltd., London, UK; Wyngaarden and Smith (eds.) (1985) *Cecil's Textbook of Medicine*, W.B. Saunders Co., Phila., Pa.; Berkow (ed.) (1982) *The Merck Manual of Diagnosis and Therapy*, Merck Sharp & Dohme Research Laboratories, West Point, Pa.; Braunwald, et al. (eds.) (1991) *Harrison's Principles of Internal Medicine*, 12th Ed., McGraw-Hill, Inc., N.Y., all of which are incorporated herein by reference.

The present invention provides methods and reagents for the treatment, prevention, and diagnosis of wounds and wound healing, e.g., burns, wounds of cartilage, nerves and spinal cord, muscle, soft tissues, blood vessels and angiogenesis, ulcers and pressure sores, bone fractures and osteoporosis, and for promoting skin growth, e.g., at harvested or donor sites used in skin grafting (see, e.g., Yamaguchi and Yoshikawa (2001) *J. Dermatol.* 28:521-534; Cairns, et al. (1993) *Arch. Surg.* 128:1246-1252; Hom, et al. (2002) *Facial Plast. Surg.* 18:41-52; Hackam and Ford (2002) *Surg. Infect.* (Larchmt.) 3(Suppl. 1):S23-S35; Oshima, et al. (2002) *Hum. Cell.* 15:118-128; Lal, et al. (2000) *Growth Horm. IGF Res.* 10 (Suppl. B):S39-S43; Rose and Herndon (1997) *Burns* 23:S19-S26; Schryvers, et al. (2000) *Arch. Phys. Med. Rehabil.* 81:1556-1562; Hidaka, et al. (2002) *Orthhop. Clin. North Am.* 33:439-446; Dagum (1998) *J. Hand Ther.* 11:111-117; Coutts, et al. (2001) *Clin. Orthop.* 391 (Suppl.):S271-S279; Larsson (2002) *Scand. J. Surg.* 91:140-146; Goldstein (2000) *Clin. Orthop.* 379 (Suppl.):S113-119; Lieberman, et al. (2002) *Mol. Therapy* 6:141-147; Tuli, et al. (2003) *Arthritis Res. Ther.* 5:235-238; Li, et al. (2003) *Microsc. Res. Tech.* 60:107-114; van Hinsbergh, et al. (2001) 936:426-437; Conway, et al. (2001) *Cardiovasc. Res.* 49:507-521).

Skin wound healing involves a number of phases: inflammation, first with neutrophil and later monocyte/macrophage inflammation, new tissue formation, including matrix formation and differentiation of a neoepithelium, and finally remodeling and maturation. The initial inflammatory phase allows clot formation, controls infection, and promotes vascularization, and produces growth factors. If not controlled properly, the inflammation can lead to pathological healing, e.g., ulcers or scars.

Fibroblasts deposit provisional matrix or granulation tissue, while the newly formed provisional matrix is later degraded in a tissue remodeling process. Degradation of extracellular matrix is mediated by proteases, such as matrix metalloproteases (MMP), gelatinase, and collagenase, as well as protease inhibitors. An imbalance in matrix formation and degradation leads, at one extreme, to chronic ulcers and, on the other extreme, to fibrosis. For example, keloids, an "overhealed response," are fibrous tissue outgrowths (Michalik, et al. (2001) *J. Cell Biol.* 154:799-814; Okada, et al. (1997) *J. Cell Biol.* 137:67-77; Fedyk, et al. (2001) *J. Immunol.* 166:5749-5755; Ravanti and Kahari (2000) *Int. J. Mol. Med.* 6:391-407; Peled, et al. (2000) *Clin. Past. Surg.* 27:489-500).

Matrix formation and reepithelialization depend on angiogenesis (Montesinos, et al. (1997) *J. Exp. Med.* 186:1615-1620; Malinda, et al. (1998) *J. Immunol.* 160:1001-1006).

Growth factors used in wound healing induce expression of anti-microbial factors, e.g., defensins, cathelicidins, secretory protease inhibitor, and gelatinase-associated lipocalin (from neutrophils) (Sorensen, et al. (2003) *J. Immunol.* 170: 5583-5589).

In wound healing, cells such as platelets, monocyte/macrophages, T cells, and other immune cells, infiltrate the wound and produce factors that regulate growth of tissue. These factors include TGF, tumor necrosis factor (TNF), IL-1, IL-4, IL-6, oncostatin M, GRO-alpha, various angiogenic factors, and chemokines. In turn, these factors stimulate, for expression of, e.g., extracellular matrix and tissue inhibitor of metalloproteases (TIMP). (Ihn and Tamaki (2000) *J. Immunol.* 165:2149-2155; Feugate, et al. (2002) *J. Cell. Biol.* 156:161-172). Myofibroblasts, cells that are fibrogenic, are important for wound closure and contraction. Disease states characterized by accumulation of myofibroblasts include pulmonary fibrosis and scleroderma (Feugate, et al. (2002) *J. Cell Biol.* 156:161-172).

Wound healing of skin and other tissues is a complex process involving proliferation and migration of immune cells, endothelial cells, fibroblasts, stromal cells, myofibroblasts, smooth muscle cells, pericytes, and keratinocytes.

Parameters used to measure healing include rate of healing, breaking strength of healed wounds, degree of epithelialization, thickness of granulation tissue, and density of extracellular matrix (Matsuda, et al. (1998) *J. Exp. Med.* 187:297-306).

Ischemia or ischemia reperfusion, as occurs with traumatic injury and "muscle unloading" (chronic bedrest), results in neutrophil infiltration, where the neutrophils often produce tissue damage in excess to the damage caused by the ischemia. Consistent with this adverse effect of neutrophils on healing is that administration of cytokine antagonists, including antagonists to IL-1 or TNF, can also improve wound healing under certain conditions, even where the cytokine is ultimately required for normal repair (see, e.g., Ley (2003) *Am. J. Physiol. Regul. Integr. Comp. Physiol.* 285:R718-R719; Graves, et al. (2001) *J. Immunol.* 167:5316-5320). The present invention provides methods using an IL-23 antagonist to inhibit neutrophil-induced tissue injury, e.g., after trauma, wounding, or prolonged bedrest.

Improper wound healing, e.g., of cutaneous wounds, can result in chronic discomfort or disfigurement, and can lead to further complications, e.g., infections or dehydration. Thus, a need exists for effective treatment, both prophylactic and curative, to alleviate the symptoms of those conditions. Alternatively, methods of diagnosis, e.g., of abnormal or modified health of those tissues will be useful. The present invention provides both.

SUMMARY OF THE INVENTION

The present invention is based, in part, upon the discovery that an IL-23 fusion protein, e.g., a fusion protein comprising the p19 subunit linked to the p40 subunit, enhanced wound healing response in various mouse models.

The invention provides a method of treating or improving healing comprising administering to a subject an effective amount of an agonist or antagonist of IL-23. Also provided is the above method, wherein the agonist or antagonist comprises a polypeptide of IL-23, or a derivative or variant thereof, a binding composition derived from an antibody that specifically binds to IL-23 or to IL-23R; or a nucleic acid encoding a polypeptide of IL-23, or a derivative or variant thereof. In addition, the invention provides the above method wherein the derivative or variant comprises an IL-23 hyperkine; wherein the agonist comprises a complex of a mature sequence of SEQ ID NO:10; and a mature sequence of SEQ ID NO:12; or the above method wherein the nucleic acid further comprises an expression vector.

In another aspect, the invention provides a method of treating or improving healing comprising administering to a subject an effective amount of an agonist or antagonist of IL-23, wherein the healing is of a skin or cutaneous wound; of an ulcer or graft; or is improper healing. Also provided is the above method wherein the treating or improving increases a pressure required to break a healed or healing wound; a stiffness of a healed or healing wound; a rate of healing of a wound; a granulation layer thickness of a healed or healing wound; recruitment of a cell to or towards a wound; or anti-microbial activity. In yet another aspect, the invention provides the above method wherein the cell is a $CD11b^+$, MHC Class $II^+$ cell; a monocyte/macrophage; a $CD31^+$ endothelial cell; or an immune cell. Also provided is the above method wherein the recruitment is in or towards a granulation tissue; wherein the increased wound breaking pressure is about a 15% or about a 20% increase in wound breaking pressure; or the increased stiffness is about a 15% or about a 20% increase in stiffness. In another embodiment, the present invention provides the above method wherein the treating or improving comprises increased angiogenesis; or immune surveillance; or the above method wherein the increased angiogenesis is mediated by ICAM-1 or -2; or the increased immune surveillance is mediated by dendritic cells.

Yet another aspect of the above invention provides a method of treating or improving healing comprising administering to a subject an effective amount of an agonist or antagonist of IL-23, wherein the treating or improving comprises increased expression of a nucleic acid or protein of a cytokine in addition to IL-23; a signaling molecule; an antimicrobial molecule; a protease or protease inhibitor; or a molecule of the extracellular matrix; or the above method wherein the cytokine nucleic acid or protein is IL-17, IL-6, IL-19, GRO-alpha, or GM-CSF; or wherein wherein the nucleic acid or protein is lactoferrin; DEC-205; CD50; nitric oxide synthase; or secretory leukoprotease inhibitor; or CD40L.

Also provided is the above method, wherein the antagonist comprises a nucleic acid; a blocking antibody to IL-23 or to IL-23R; or a soluble receptor derived from an extracellular part of IL-23R; the above method wherein the nucleic acid comprises an anti-sense nucleic acid; or interference RNA.

Yet another aspect of the present invention provides an agonist of IL-23 derived from the binding site of an antibody that specifically binds to an IL-23 receptor; the above agonist that is a polyclonal antibody; a monoclonal antibody; an Fab, Fv, or $F(ab')_2$ fragment; humanized; a peptide mimetic; or detectably labeled. In another embodiment, the present invention provides the above agonist comprising a complex of a polypeptide of the mature sequence of SEQ ID NO:10 and a polypeptide of the mature sequence of SEQ ID NO:12; the above agonist comprising a complex of two polypeptides of the mature sequence of SEQ ID NO: 10 and two polypeptides of the mature sequence of SEQ ID NO:12. Moreover the invention provides the above agonist wherein contact of the agonist to a cell expressing hIL-23R and hIL-12beta1 results in an increase in proliferation of the cell. Also provided is a kit comprising the above agonist and a compartment; or instructions for use or disposal. Also provided is a nucleic acid encoding an agonist of IL-23 derived from the binding site of an antibody that specifically binds to an IL-23 receptor.

DETAILED DESCRIPTION OF THE PREFERRED EMBODIMENTS

All references cited herein are incorporated herein by reference to the same extent as if each individual publication or patent application was specifically and individually indicated to be incorporated by reference.

As used herein, including the appended claims, the singular forms of words such as "a," "an," and "the," include their corresponding plural references unless the context clearly dictates otherwise.

I. GENERAL

Interleukin-23 (IL-23) is a heterodimeric cytokine composed of a novel p19 subunit (a.k.a. IL-B30) and the p40 subunit of IL-12 (Oppmann, et al., supra). The p19 subunit was identified during a computational search for members of the IL-6 helical cytokine family characterized by their unique four α-helix bundle. Genetic analysis of the family, of which oncostatin-M, IL-11, cardiotrophin-1, and leukaemia inhibitory factor are members, reveals the closest evolutionary neighbor of p19 to be the p35 subunit of IL-12. Like p35, p19 requires co-expression of p40 for biological activity (Wiekowski, et al. (2001) *J. Immunol.* 166:7563-7570). The IL-23 receptor (IL-23R) comprises a novel receptor subunit (IL-23R), that binds p19, and IL-12Rβ1, that binds p40 (Parham, et al. (2002) *J. Immunol.* 168:5699-5708). These two receptor subunits form the functional signaling complex and are expressed on $CD4^+CD45Rb^{lo}$ memory T cells as well as interferon-gamma (IFNgamma) activated bone marrow macrophages (Parham, et al., supra).

Preliminary characterization of IL-23 suggests that it has potent effects on memory T cells from both humans and mice, as measured by proliferation and IFNgamma production. Consistent with the immunostimulatory properties of IL-23, mice in which haematopoetic cells constitutively express transgenic p19 have widespread multi-organ inflammation that results in premature death (Wiekowski, et al., supra). The inflammatory disease is characterized by intense macrophage infiltration, neutrophilia, and elevated levels of proinflammatory monokines such as IL-1 and TNF, suggesting that IL-23 may also act on myeloid cells.

Recent studies analyzing the necessity of IL-12 in resistance to infectious diseases have yielded divergent results, depending on whether $p35^{-/-}$ or $p40^{-/-}$ mice are used. The former, which specifically lack IL-12 but express IL-23, are resistant to infection, whereas the latter, unable to express both IL-12 and IL-23, are more susceptible.

Transgenic mice deficient for the p19 subunit of IL-23 (IL-23p19) were resistant to EAE, a CNS autoimmune disease mediated by TH1 cells and inflammatory macrophages, while wild-type and heterozygous p19 control mice were highly susceptible. Mice deficient in the p40 subunit of IL-12 (IL-12p40 deficient mice) were also resistant to EAE, while mice deficient in the p35 subunit of IL-12 (IL-12p35 deficient mice) were highly susceptible to EAE. This is indicative of a role of IL-23 in the induction of EAE.

p19 deficient mice had a notable altered wound healing response following subcutaneous injection of an oil emulsion in mice. The p19 deficient mice were also defective in a variety of mouse disease models that required monocyte/macrophage activation. Monocytes/macrophages are known to stimulate wound repair, see, e.g., Schaffer and Nanney (1996) *Intl. Rev. Cytol* 169:151-181. In particular, it is shown below that delivery of IL-23 polypeptide into mouse skin could attract $CD11b^+$/Class $II^+$ activated monocyte/macrophage populations.

II. DEFINITIONS

"Agonist of IL-23" and "IL-23 agonist" encompasses an agonistic antibody that specifically binds to IL-23 receptor (IL-23R) and increases the signaling properties of IL-23R. Agonist of IL-23 also encompasses an agonistic antibody that specifically binds to the complex of IL-23R and IL-12Rbeta1.

A "blocking antibody" encompasses, e.g., an antibody that specifically binds to IL-23 and prevents or impairs signaling mediated by IL-23 and IL-23R. A blocking antibody also encompasses an antibody that specifically binds to IL-23R and prevents or impairs signaling mediated by IL-23R, or mediated by IL-23 and IL-23R.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157:105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

The phrase "effective amount" means an amount sufficient to ameliorate a symptom or sign of the medical condition. Typical mammalian hosts will include mice, rats, cats, dogs, and primates, including humans. An effective amount for a particular patient may vary depending on factors such as the condition being treated, the overall health of the patient, the method route and dose of administration and the severity of side affects. When in combination, an effective amount is in ratio to a combination of components and the effect is not limited to individual components alone.

An "endpoint" for assessing or diagnosing improved healing, e.g., wound healing, includes, without limitation: wound breaking pressure; stiffness, looseness; immune surveillance; angiogenesis; wound-related anti-microbial activity; inflammation, e.g., by neutrophils; degree of expression of genes or polypeptides indicative of inflammation, angiogenesis, reepithelialization, anti-microbial action, and remodeling, e.g., matrix formation, matrix breakdown, or granulization.

As determined by a suitable endpoint, the present invention provides a method to improve healing by 10% or more, more generally by 15% or more, most generally by 20% or more, typically 25% or more, more typically by 30% or more, most typically by 35% or more, often by 40% or more, more often by 50% or more, most often by 60% or more, usually by 70% or more, more usually by 80% or more, most usually by 90% or more, ideally by 100% (i.e., 2-fold) or more, more ideally by 4-fold or more, and most ideally by 8-fold or more. As determined by a suitable endpoint, the present invention also provides a method to improve healing by about 10%, more generally by about 15%, most generally by about 20%, typically about 25%, more typically by about 30%, most typically by about 35%, often by about 40%, more often by about 50%, most often by about 60%, usually by about 70%, more usually by about 80%, most usually by about 90%, ideally by about 100% (i.e., 2-fold), more ideally by about 4-fold, and most ideally by about 8-fold.

"Improper wound healing" encompasses the absence or abnormally slow progression of the healing of a wound, e.g., delayed re-epithelialization. Improper wound healing can be found, e.g., in diabetic ulcers and abscesses, pressure ulcers, infected wounds, burns, advanced age, inadequate perfusion, and obesity. Improper wound healing also encompasses injuries leading to scars or to persistent infections, see, e.g., Singer and Clark (1999) *New Engl. J. Med.* 341:738-746; Calhoun, et al. (2002) *Adv. Skin Wound Care* 15:31-45; Rico, et al. (2002) *J. Surg. Res.* 102:193-197; Thomas (2001) *Cleve. Clin. J. Med.* 68:704-722; Ashcroft, et al. (2002) *Biogerontology* 3:337-345; Thomason (1999) *Home Care Provid.* 4:156-161; Gallagher (1997) *Ostomy. Wound Manage.* 43:18-27.

Parameters and endpoints used to assess wound healing and response to therapeutic, pharmacological, and diagnostic agents, include a number of histological, physiological, and biochemical parameters, e.g., infiltration, activation, or differentiation of neutrophils, monocytes, and macrophages, e.g., differentiation of monocytes to reparative macrophages, and appearance of new stroma, blood vessels, and nerves. Suitable parameters also include expression levels of signaling agents, e.g., transforming growth factor, interleukin-1, and insulin-like growth factor. Measures of epithelization, e.g., rate and migration of epidermal cells, granulation thickness, degradation and maturation of extracellular matrix, e.g., provisional matrix versus collagenous matrix, wound strength (breaking strength), and fibroblast proliferation rate and phenotype, are also suitable parameters. Increased granulation tissue thickness can resulting stronger healed wounds (see, e.g., Singer and Clark, supra, Werner and Grose (2002) *Physiol. Rev.* 83:835-870; Matsuda, et al. (1998) *J. Exp. Med.* 187:297-306; Wankell, et al. (2001) *EMBO J.* 20:5361-5372).

A composition that is "labeled" is detectable either directly or indirectly by, e.g., spectroscopic, photochemical, biochemical, metabolic, immunochemical, isotopic, or chemical methods. For example, useful labels include epitope tags, fluorettes, $^{32}$P, $^{33}$P, $^{35}$S, $^{14}$C, $^{3}$H, $^{125}$I, stable isotopes, fluorescent compounds, electron-dense reagents, substrates, or enzymes, e.g., as used in enzyme-linked immunoassays, see, e.g., Invitrogen (2002) *Catalogue*, Carlsbad, Calif.; Molecular Probes (2002) *Catalogue*, Molecular Probes, Eugene, Oreg.; Rozinov and Nolan (1998) *Chem. Biol.* 5:713-728.

Increase in "anti-microbial activity" encompasses an increase in expression, concentration, or level of a mediator of anti-microbial activity, both in the presence and absence of demonstrated reduction in biological activity, concentration, population, or number of a microbe in contact with a human or animal subject or host. The mediator of anti-microbial activity can be, e.g., an immune cell responsive to a bacterial, viral, fungal, or protozoal, or parasitic antigen, or an anti-microbial molecule, such as a defensin. "Anti-microbial activity" embraces, e.g., phagocytosis and any activity that is generally or usually associated with phagocytosis, e.g., exposure of a microbe to toxic oxygen. "Anti-microbial activity" also encompasses an change in expression, concentration, or level of a cell, gene, protein, or small molecule that is generally or usually associated with anti-microbial action, e.g., an increase in expression of a neutrophil gene. "Anti-microbial activity" is not limited to an increase in expression, i.e., it also encompasses a decrease in expression, where that decrease promotes anti-microbial activity.

"Proliferation" or "rate of proliferation" can be measured, e.g., by assessing the increase in cell number over a predetermined period or interval of time, or by the number or proportion of cells in S phase at any given point in time.

III. AGONISTS AND ANTAGONISTS

The present invention provides methods of using IL-23 agonists including the full length cytokine protein (SEQ ID NO: 2 or 4). Also provided is a fusion protein, also known as "IL-23 hyperkine" (SEQ ID NO: 6 or 8), comprising p19 linked to p40 with a FLAG sequence as described for IL-6 in, e.g., Oppmann, et al., supra; Fischer, et al. (1997) *Nature Biotechnol.* 15:142-145; Rakemann, et al. (1999) *J. Biol. Chem.* 274:1257-1266; and Peters, et al. (1998) *J. Immunol.* 161:3575-3581, thereof. The invention also provides agonistic anti-IL-23R antibodies that are agonistic to the IL-23 receptor, e.g., antibodies that stimulate the IL-23 receptor in the absence or presence of IL-23.

Peptides of those sequences, or variants thereof, will be used to induce receptor signaling. Also contemplated are small molecules which also induce receptor signaling. Agonists of the present invention will be useful in the treatment of various inflammatory skin disorders, including but not limited to wound healing, skin disorders associated with impaired recruitment of myeloid/monocyte cells.

The invention provides IL-23 antagonists, e.g., a blocking antibody that binds to IL-23, a blocking antibody that binds to IL-23R, a soluble receptor based on the extracellular portion of IL-23R, and nucleic acids. The IL-23 antagonists of the present invention encompass nucleic acids that are anti-sense nucleic acids and RNA interference nucleic acids (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Nucl. Acid Drug Devel.* 13:169-189).

III. ANTIBODIES AND RELATED REAGENTS

Antibodies and binding compositions derived from an antigen-binding site of an antibody are provided. These include humanized antibodies, monoclonal antibodies, polyclonal antibodies, and binding fragments, such as Fab, F(ab)$_2$, and Fv fragments, and engineered versions thereof. The antibody or binding composition may be agonistic or antagonistic. Antibodies that simultaneously bind to a ligand and receptor are contemplated. Monoclonal antibodies will usually bind with at least a $K_D$ of about 1 mM, more usually at least about 300 μM, typically at least about 100 μM, more typically at least about 30 μM, preferably at least about 10 μM, and more preferably at least about 3 μM or better.

Monoclonal, polyclonal, and humanized antibodies can be prepared. See, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, N.Y.; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378).

Single chain antibodies, single domain antibodies, and bispecific antibodies are described, see, e.g., Malecki, et al. (2002) *Proc. Natl. Acad. Sci. USA* 99:213-218; Conrath, et al. (2001) *J. Biol. Chem.* 276:7346-7350; Desmyter, et al. (2001) *J. Biol. Chem.* 276:26285-26290, Kostelney, et al. (1992) *J. Immunol.* 148:1547-1553; U.S. Pat. Nos. 5,932,448; 5,532, 210; 6,129,914; 6,133,426; 4,946,778.

The invention also encompasses deamidated binding compositions, e.g., antibodies, and methods of using deamidated binding compositions (see, e.g., Zhang and Czupryn (2003) *J.*

Pharm. Biomed. Anal. 30:1479-1490; Perkins, et al. (2000) Pharm. Res. 17:1110-1117; Lehrman, et al. (1992) J. Protein Chem. 11:657-663).

Antigen fragments may be joined to other materials, such as fused or covalently joined polypeptides, to be used as immunogens. An antigen and its fragments may be fused or covalently linked to a variety of immunogens, such as keyhole limpet hemocyanin, bovine serum albumin, or ovalbumin (Coligan, et al. (1994) Current Protocols in Immunol., Vol. 2, 9.3-9.4, John Wiley and Sons, New York, N.Y.). Peptides of suitable antigenicity can be selected from the polypeptide target, using an algorithm, such as those of Parker, et al. (1986) Biochemistry 25:5425-5432; Welling, et al. (1985) FEBS Lett. 188:215-218; Jameson and Wolf (1988) Cabios 4:181-186; or Hopp and Woods (1983) Mol. Immunol. 20:483-489.

Purification of antigen is not necessary for the generation of antibodies. Immunization can be performed by DNA vector immunization. See, e.g., Wang, et al. (1997) Virology 228:278-284. Alternatively, animals can be immunized with cells bearing the antigen of interest. Splenocytes can then be isolated from the immunized animals, and the splenocytes can fused with a myeloma cell line to produce a hybridoma. Resultant hybridomas can be screened for production of the desired antibody by functional assays or biological assays, that is, assays not dependent on possession of the purified antigen. Immunization with cells may prove superior for antibody generation than immunization with purified antigen (Meyaard, et al. (1997) Immunity 7:283-290; Wright, et al. (2000) Immunity 13:233-242; Preston, et al. (1997) Eur. J. Immunol. 27:1911-1918; Kaithamana, et al. (1999) J. Immunol. 163:5157-5164).

Antibody affinity, i.e., antibody to antigen binding properties can be measured, e.g., by surface plasmon resonance or enzyme linked immunosorbent assay (ELISA) (see, e.g., Maynard and Georgiou (2000) Annu. Rev. Biomed. Eng. 2:339-376; Karlsson, et al. (1991) J. Immunol. Methods 145: 229-240; Neri, et al. (1997) Nat. Biotechnol. 15:1271-1275; Jonsson, et al. (1991) Biotechniques 11:620-627; Friguet, et al. (1985) J. Immunol. Methods 77:305-319; Hubble (1997) Immunol Today 18:305-306).

Antibodies of the present invention will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) Thromb. Haemost. 85:379-389; Yang, et al. (2001) Crit. Rev. Oncol. Hematol. 38:17-23; Carnahan, et al. (2003) Clin. Cancer Res. (Suppl.) 9:3982s-3990s; Wilchek, et al. (1984) Meth. Enzymol. 104:3-55).

Antibodies to IL-23R, where the anti-IL-23R antibody has substantially the same nucleic acid and amino acid sequence as those recited herein, but possessing substitutions that do not substantially affect the functional aspects of the nucleic acid or amino acid sequence, are within the definition of the contemplated invention. Variants with truncations, deletions, additions, and substitutions of regions which do not substantially change the biological functions of these nucleic acids and polypeptides are also within the definition of the contemplated invention.

A humanized antibody encompasses a human antibody, antibody fragment, single chain antibody, and the like, that has one or more amino acid residues introduced into it from a source which is non-human (import antibody). The amino acids used for grafting may comprise the entire variable domain of the source, one or more of the complementary determining regions (CDRs) of the source, or all six of the CDRs of the source antibody. With grafting of the import amino acids or polypeptide regions on to the host antibody, the corresponding amino acids or regions of the host antibody are generally removed. A humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the framework regions are those of a human immunoglobulin consensus sequence. The framework regions and CDRs are highly conserved in sequence and conformation and can be accurately predicted, e.g., for use in grafting CDRs into an acceptor human antibody framework. CDR regions can be grafted into a naturally occurring human acceptor framework, or in a consensus framework derived from many human antibodies. A number of human variable light ($V_L$) and variable heavy ($V_H$) consensus sequences have been identified. For humanization, a chain of the mouse antibody can be compared with the available human framework chains, where the human chain of closest homology is chosen for grafting (see, e.g., Maynard and Georgiou, supra; Li, et al. (2002) Immunol. Revs. 190:53-68; Co, et al. (1991) Proc. Natl. Acad. Sci. USA 88:2869-2873; Sims, et al. (1993) J. Immunol. 151:2296-2308; Sato, et al. (1994) Mol. Immunol. 31:371-381; Morea, et al. (2000) Methods 20:267-279; Kabat et al. (1991) Sequences of Proteins of Immunological Interest, $5^{th}$ ed., 4 vol., U.S. Department of Health Human Services, NIH, USA; U.S. Pat. No. 6,538,111, issued to Koike, et al.; U.S. Pat. No. 6,329,511, issued to Vasquez, et al.).

The humanized antibody of the present invention also encompasses substitutions, deletions, and/or insertions, using standard techniques of site-directed mutagenesis, e.g., those used for alanine scanning, see, e.g., Jin and Wells (1994) Protein Sci. 3:2351-2357; Cunningham and Wells (1997) Curr. Opin. Struct. Biol. 7:457-462; Jones, et al. (1998) J. Biol. Chem. 273:11667-11674; U.S. Pat. No. 4,816,567 issued to Cabilly, et al.

Embodiments of the present invention encompass fusion proteins, purification tags, and epitope tag, at an N-terminus, C-terminus, or positions within the polypeptide, e.g., FLAG tag and GSH-S transferase fusion protein. Amino acid changes can alter, add, or eliminate post-translational processes of the agonist anti-IL-23R antibody, e.g., sites for O- and N-glycosylation, and positions of cysteine residues used for disulfide formation, see, e.g., Wright and Morrison (1997) Trends Biotechnol. 15:26-32; Kunkel, et al. (2000) Biotechnol. Prog. 16:462-470.

Binding properties of the humanized antibody can be improved by the following procedure, e.g., involving site-directed mutagenesis. Computer modeling allows visualization of which mouse framework amino acid residues are likely to interact with mouse CDRs. These "contacting" mouse framework amino acids are then superimposed on the homologous human framework. Where the superimposition indicates that the mouse "contacting" framework amino acid is different from the corresponding human framework amino acid, human amino acid is changed to the corresponding mouse framework amino acid. "Contact" means interchain contact between a light chain and heavy chain, where, e.g., the amino acids are predicted to be within about 3 Angstroms of each other.

Site-directed mutagenesis can also be desirable where the amino acid of the human framework is rare for that position and the corresponding amino acid in the mouse immunoglobin is common for that position in human immunoglobin sequences. Here, the human framework amino acid can be mutated to the corresponding donor framework amino acid, see, e.g., U.S. Pat. No. 6,407,213, issued to Carter et al.; U.S. Pat. No. 6,180,370, issued to Queen, et al., Jung, et al. (2001) *J. Mol. Biol.* 309:701-716.

The humanized antibody can comprise at least a portion of an immunoglobulin constant region (Fc), e.g., of a human immunoglobulin. The antibody can optionally include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Standard methods can be used to improve, or remove, effector function. Effector function includes binding to FcRn, FcgammaR, and complement. Half-life can be improved, e.g., by using human IgG2 or IgG4 subclasses or by altering residues in the hinge region (see, e.g., Clark (2000) *Immunol Today* 21:397-402; Presta, et al. (2002) *Biochem. Soc. Trans.* 30:487-490; Morea, et al. (2000) *Methods* 20:267-279).

The CDR and framework regions of the humanized antibody need not correspond precisely to the import or host sequences, e.g., these sequences can be mutagenized by substitution, insertion or deletion of at least one residue so that the residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%.

Ordinarily, amino acid sequence variants of the humanized anti-IL-23R antibody will have an amino acid sequence having at least 75% amino acid sequence identity with the original humanized antibody amino acid sequences of either the heavy or the light chain (e.g. as in SEQ ID NOs:2 and 4), more preferably at least 80%, more preferably at least 85%, more preferably at least 90%, and most preferably at least 95%. Identity or homology with respect to this sequence is defined herein as the percentage of amino acid residues in the candidate sequence that are identical with the humanized anti-IL-23R residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

An alternative to humanization is to use human antibody libraries displayed on phage or human antibody libraries contained in transgenic mice (see, e.g., Vaughan, et al. (1996) *Nat. Biotechnol.* 14:309-314; Barbas (1995) *Nature Med.* 1:837-839; de Haard, et al. (1999) *J. Biol. Chem.* 274:18218-18230; McCafferty et al. (1990) *Nature* 348:552-554; Clackson et al. (1991) *Nature* 352:624-628; Marks et al. (1991) *J. Mol. Biol.* 222:581-597; Mendez, et al. (1997) *Nature Genet.* 15:146-156; Hoogenboom and Chames (2000) *Immunol Today* 21:371-377; Barbas, et al. (2001) *Phage Display: A Laboratory Manual*, Cold Spring Harbor Laboratory Press, Cold Spring Harbor, N.Y.; Kay, et al. (1996) *Phage Display of Peptides and Proteins: A Laboratory Manual*, Academic Press, San Diego, Calif.; de Bruin, et al. (1999) *Nat. Biotechnol.* 17:397-399).

IV. NUCLEIC ACIDS, VECTORS, AND PROTEIN PURIFICATION

An "expression vector" is a nucleic acid construct, generated recombinantly or synthetically, with one or more predetermined nucleic acid elements that permit transcription of a particular nucleic acid. Typically, the expression vector includes a nucleic acid to be transcribed operably linked to a promoter.

The light chain and heavy chain of the agonistic anti-IL-23R antibody can be encoded by one nucleic acid, where expression of the light chain is operably linked to a first promoter, and where expression of the heavy chain is operably linked to a second promoter. Alternatively, both light and heavy chains can be encoded by one nucleic acid, where expression of both chains is operably linked to one promoter. The nucleic acid or nucleic acids encoding the light chain and the heavy chain can be provided as one or as two vectors. The methods of the present invention encompass incorporation of the one or two vectors into the genome of a host cell (see, e.g., Chadd and Chamow (2001) *Curr. Opin. Biotechnol.* 12:188-194; Houdebine (2000) *Transgenic Res.* 9:305-320; Stoger, et al. (2002) *Curr. Opin. Biotechnol.* 13:161-166).

The nucleic acid encoding the light chain can further comprise a first vector, while the nucleic acid encoding the heavy chain can further comprise a second vector. Alternatively, one vector may comprise the nucleic acids encoding the light chain and the heavy chain.

For long-term or scaled-up expression of the agonistic anti-IL-23R antibody, one vector, containing the nucleic acids encoding both the light chain and the heavy chain, can be incorporated into the host genome, e.g., where incorporation is at one point or a plurality of points in the host genome. Coexpression of the light chain and heavy chain in a host cell produces a soluble antibody. The host cell can be, e.g., a mammalian, transformed or immortalized, insect, plant, yeast, or bacterial cell. The host cell may further comprise a transgenic animal. Combinations of the above embodiments are contemplated, e.g., where the light chain is simultaneously expressed by a vector that is incorporated in the host cell's genome and by a vector that is not incorporated in the genome.

Purification of an antibody, or fragments thereof, can involve ion exchange chromatography, immunoprecipitation, epitope tags, affinity chromatography, high pressure liquid chromatography, and use of stabilizing agents, detergents or emulsifiers (Dennison and Lovrien (1997) *Protein Expression Purif.* 11: 149-161; Murby, et al. (1996) *Protein Expression Purif.* 7:129-136; Ausubel, et al. (2001) *Curr. Protocols Mol. Biol., Vol.* 3, John Wiley and Sons, New York, N.Y., pp. 17.0.1-17.23.8; Rajan, et al. (1998) *Protein Expression Purif.* 13:67-72; Amersham-Pharmacia (2001) *Catalogue*, Amersham-Pharmacia Biotech, Inc., pp. 543-567, 605-654; Gooding and Regnier (2002) *HPLC of Biological Molecules*, 2$^{nd}$ ed., Marcel Dekker, N.Y.).

V. KITS

This invention contemplates an agonistic anti-IL23R antibody, fragments thereof, nucleic acids encoding an agonistic anti-IL-23R antibody, or fragments thereof, in a diagnostic kit. Encompassed is the use of binding compositions, including antibodies or antibody fragments, for the detection of IL-23R and metabolites and breakdown products thereof, and for the detection of IL-23R-dependent activities, e.g., biochemical or cellular activity. Conjugated antibodies are useful for diagnostic or kit purposes, and include antibodies coupled with a label or polypeptide, e.g., a dye, isotopes, enzyme, or metal, see, e.g., Le Doussal, et al. (1991) *J. Immunol.* 146:169-175; Gibellini, et al. (1998) *J. Immunol.* 160: 3891-3898; Hsing and Bishop (1999) *J. Immunol.* 162:2804-2811; Everts, et al. (2002) *J. Immunol.* 168:883-889.

The invention provides a kit, where the kit comprises a compartment containing an agonistic anti-IL-23R antibody, an antigenic fragment thereof, or a nucleic acid encoding an agonistic anti-IL-23R antibody, or a fragment thereof. In another embodiment the kit has a compartment, a nucleic acid, e.g., a probe, primer, or molecular beacon, see, e.g., Zammatteo, et al. (2002) *Biotech. Annu. Rev.* 8:85-101; Klein (2002) *Trends Mol. Med.* 8:257-260.

The kit may comprise, e.g., a reagent and a compartment, a reagent and instructions for use, or a reagent with both a compartment and instructions for use. A kit for determining the binding of a test compound, e.g., acquired from a biological sample or from a chemical library, can comprise a control compound, a labeled compound, and a method for separating free labeled compound from bound labeled compound. Diagnostic assays can be used with biological matrices such as live cells, cell extracts and lysates, fixed cells, cell cultures, bodily fluids, or forensic samples. Various assay formats exist, such as radioimmunoassays (RIA), ELISA, and lab on a chip (U.S. Pat. Nos. 6,176,962 and 6,517,234).

The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

VI. DIAGNOSTIC USES; THERAPEUTIC COMPOSITIONS; METHODS

The present invention provides methods for the treatment and diagnosis of healing, improper healing, wound healing, and improper wound healing, e.g., of the skin. Provided are methods of improving normal wound healing, e.g., by improving the rate of healing, and of treating improper wound healing, e.g., wounds characterized by ulcers or excess fibrosis. Moreover, the invention provides methods of treating and preventing wound-related infections.

Gene therapy of skin disorders may be performed using a variety of methods. Delivery vehicles are well described in the art, see, e.g., Boulikas (1998) *Gene Therapy and Molecular Biology, Vol.* 1, Gene Therapy Press, Palo Alto, Calif.; Jolly, et al. (1994) *Cancer Gene Therapy* 1:51-64; Kimura, et al. (1994) *Human Gene Therapy* 5:845-852; and Kaplitt, et al. (1994) *Nat. Genetics* 6:148-153.

To prepare pharmaceutical or sterile compositions including a cytokine or a small molecule agonist, the entity is admixed with a pharmaceutically acceptable carrier or excipient which is preferably inert. Preparation of such pharmaceutical compositions is known in the art, see, e.g., *Remington's Pharmaceutical Sciences and U.S. Pharmacopeia: National Formulary*, Mack Publishing Company, Easton, Pa. (1984).

Cytokines are normally administered parentally, preferably intravenously. Since such proteins or peptides may be immunogenic they are preferably administered slowly, either by a conventional IV administration set or from a subcutaneous depot, e.g. as taught by Tomasi, et al, U.S. Pat. No. 4,732,863. Means to minimize immunological reactions may be applied. Small molecule entities may be orally active. For treatment of skin disorders, the present invention may also be administered topically, see, e.g., Gilman, et al. (eds.) (1990) *Goodman and Gilman's: The Pharmacological Bases of Therapeutics, 8th ed.*, Pergamon Press; and *Remington's Pharmaceutical Sciences, 17th ed.* (1990), Mack Publishing Co., Easton, Pa.

Parenteral therapeutics may be administered in aqueous vehicles such as water, saline, or buffered vehicles with or without various additives and/or diluting agents. Alternatively, a suspension, such as a zinc suspension, can be prepared to include the peptide. Such a suspension can be useful for subcutaneous (SQ) or intramuscular (IM) injection, see, e.g., Avis, et al. (eds.) (1993) *Pharmaceutical Dosage Forms: Parenteral Medications 2d ed.*, Dekker, N.Y.; Lieberman, et al. (eds. 1990) *Pharmaceutical Dosage Forms: Tablets 2d ed.*, Dekker, N.Y.; Lieberman, et al. (eds. 1990) *Pharmaceutical Dosage Forms: Disperse Systems* Dekker, N.Y.; Fodor, et al. (1991) *Science* 251:767-773, Coligan (ed.) Current Protocols in Immunology; Hood, et al. Immunology Benjamin/Cummings; Paul (ed.) Fundamental Immunology; Academic Press; Parce, et al. (1989) *Science* 246:243-247; Owicki, et al. (1990) *Proc. Natl. Acad. Sci. USA* 87:4007-4011; and Blundell and Johnson (1976) *Protein Crystallography*, Academic Press, New York.

Selecting an administration regimen for a therapeutic depends on several factors, including the serum or tissue turnover rate of the entity, the level of symptoms, the immunogenicity of the entity, and the accessibility of the target cells, timing of administration, absorption through epithelial layers, etc. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of cytokine or small molecules are determined using standard methodologies.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscularly, intracerebrally, or by inhalation. A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg, see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg.*

Psych. 67:451-456; Portielji, et al. (2003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

The present invention also provides for administration of biologics in combination with known therapies, e.g., steroids, particularly glucocorticoids, which alleviate the symptoms, e.g., associated with inflammation, or antibiotics or anti-infectives. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day. Suitable dose combinations with antibiotics, anti-infectives, or anti-inflammatories are also known.

The present invention provides agonists and antagonists of IL-23 for modulating genes relating to healing, e.g., wound healing. Also provided are methods of diagnosis of healing, e.g., involving detecting expression or changes in expression of IL-23 modulated genes and gene products. These genes and gene products include, e.g., nitric oxide synthase 2 (NOS2), lactoferrin, IL-19, DEC-205, CD50 (ICAM-2), IL-25, TNFSF7 (CD27L), eosinophilic basic protein, and others.

The invention provides a method to modulate expression of MMP-7, e.g., for the treatment of wound healing. Matrix proteolysis is a hallmark of inflammation. Matrilysin, a metalloprotease, is used in wound repair (see, e.g., Parks, et al. (2001) *Chest* 120:36S-41S; Wilson, et al. (1999) *Science* 286:113-117).

The present invention provides methods for modulating activities and proteins relating to neutrophils, such as neutrophil chemoattractants and proteins and metabolites expressed by neutrophils. IL-23 stimulates IL-17 expression which, in turn, stimulates production of chemokines that attract neutrophils. Increased expression or activity of neutrophil response, lactoferrin, IL-17, IL-6, and nitric oxide, are found in a number of inflammatory conditions, and can play a role in modulating wound healing (see, e.g., Tsokos, et al. (2002) *Virchows Arch.* 441:494-499; Linden (2001) *Int. Arch. Allergy Immunol.* 126:179-184; Sheppard (2002) *Chest* 121:21S-25S; Redington (2000) *Monaldi Arch. Chest Dis.* 55:317-323; Vignola, et al. (2001) *Curr. Allergy Asthma Rep.* 1:108-115).

Provided are methods of modulating expression of lactoferrin, a protein produced by neutrophils (see, e.g., Boyton, et al. (2002) *Brit. Medical Bull.* 61:1-12; Singh, et al. (2002) *Nature* 417:552-555; Gomez, et al. (2002) *Infect. Immun.* 70:7050-7053).

Provided are methods for modulating expression of neutrophil elastase, e.g., for modulating wound healing (see, e.g., Tkalcevic, et al. (2000) *Immunity* 12:201-210; Aprikyan, et al. (2001) *Curr. Opinion Immunol* 13:535-538; Tremblay, et al. (2003) *Curr. Opin. Investig. Drugs* 4:556-565; Lee, et al. (2001) *Curr. Opinion Crit. Care* 7:1-7; Shapiro (2002) *Am. J. Respir. Cell Mol Biol.* 26:266-268).

Also provided are methods to modulate neutrophil attractants for promoting wound healing, e.g., IL-17, nitric oxide, and GRO-alpha. IL-17 modulates neutrophil recruitment (see, e.g., Ye, et al. (2001) *J. Exp. Med.* 194:519-527; Ye, et al. (2001) *Am. J. Respir. Cell Mol. Biol.* 25:335-340). Nitric oxide, synthesized by nitric oxide synthase, can promote wound healing, e.g., by attracting monocytes and neutrophils to the wound, see, e.g., Schwentker, et al. (2002) *Nitric Oxide* 7: 1-10; MacMicking, et al. (1997) *Annu. Rev. Immunol* 15:323-350. CXCL-1 (a.k.a. GRO-alpha) promotes wound healing, e.g., by attracting neutrophils to wounds and stimulating keratinocyte proliferation and angiogenesis (see, e.g., Gillitzer, et al. (2001) *J. Leukoc. Biol.* 69:513-521; Li and Thornhill (2000) *Cytokine* 12:1409-1413).

IL-6 promotes the healing of injuries, e.g., skin wounds, see, e.g., Gallucci, et al. (2001) *J. Interferon Cytokine Res.* 21:603-609; Sugawara, et al. (2001) *Cytokine* 15:328-336; Erdag, et al. (2002) *Ann. Surg.* 235:113-124; Nadeau, et al. (2002) *Microbes Infect.* 4:1379-1387; Imanishi, et al. (2000) *Prog. Retin. Eye Res.* 19:113-129; Gregory, et al. (1998) *J. Immunol.* 160:6056-6061.

Interferon-gamma (IFNgamma) mediates proper wound healing, e.g., by modulating actin and collagen content, contractile capacity, and scar formation, see, e.g., Moulin, et al. (1998) *Exp. Cell Res.* 238:283-293; Ahdieh, et al. (2001) *Am. J. Physiol. Cell Physiol.* 281:C2029-C2038; Cornelissen, et al. (2000) *J. Dent. Res.* 79:1782-1788; Shtrichman, et al. (2001) *Curr. Opin. Microbiol.* 4:251-259; Ikeda, et al. (2002) *Cytokine Growth Factor Rev.* 13:95-109; Rottenberg, et al. (2002) *Curr. Opin. Immunol* 14:444-451).

IFNgamma production is stimulated by CD27 (a.k.a. TNFRSF7). CD27 also stimulates cell proliferation and is implicated in the activation and development of T cells, and in T cell-dependent antibody production, including IgE production, by B cells (see, e.g., Takeda, et al. (2000) *J. Immunol.* 164:1741-1745; Nagumo, et al. (1998) *J. Immunol.* 161: 6496-6502; Tomiyama, et al. (2002) *J. Immunol.* 168:5538-5550; Busse and Lemanske (2001) *New Engl. J. Med.* 344: 350-362).

MUC5ac serves a number of biological functions, including wound healing, see, e.g., Dohrman, et al. (1998) *Biochim. Biophys. Acta* 1406:251-259; Rose, et al. (2000) *J. Aerosol. Med.* 13:245-261; Rogers (2000) *Monaldi Arch. Chest Dis.* 55:324-332; Enss, et al. (2000) *Inflamm. Res.* 49:162-169.

The broad scope of this invention is best understood with reference to the following examples, which are not intended to limit the inventions to the specific embodiments.

EXAMPLES

I. General Methods

Standard methods of biochemistry and molecular biology are described or referenced, e.g., in Maniatis, et al. (1982) *Molecular Cloning, A Laboratory Manual*, Cold Spring Harbor Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.; Innis, et al. (eds.) (1990) *PCR Protocols: A Guide to Methods and Applications*, Academic Press, N.Y. Standard methods are also found in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4). Methods for producing fusion proteins are described. See, e.g., Invitrogen (2002) *Catalogue*, Carlsbad, Calif.; Amersham Pharmacia Biotech (2002), *Catalogue*, Piscataway, N.J.; Liu, et al. (2001) *Curr. Protein Pept. Sci.* 2:107-121; Graddis, et al. (2002) *Curr. Pharm. Biotechnol.* 3:285-297. Standard methods of histology are described (Carson (1997) *Histotechnology: A Self-Instructional Text*, $2^{nd}$ ed., Am. Soc. Clin. Pathol. Press, Chicago, Ill.; Bancroft and Gamble (eds.) (2002) *Theory and Practice of Histological Techniques*, 5th ed., W.B. Saunders Co., Phila., Pa.).

Methods for flow cytometry, including fluorescence activated cell sorting (FACS), are available, see, e.g., Owens, et al. (1994) *Flow Cytometry Principles for Clinical Laboratory Practice*, John Wiley and Sons, Hoboken, N.J.; Givan (2001) *Flow Cytometry*, 2nd ed.; Wiley-Liss, Hoboken, N.J.; Shapiro (2003) *Practical Flow Cytometry*, John Wiley and Sons, Hoboken, N.J.

Standard methods of histology of the immune system are described, see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Methods for antibody production and modification are described in, e.g., Coligan, et al. (2001) *Current Protcols in Immunology*, Vol. 1, John Wiley and Sons, Inc., New York; Harlow and Lane (1999) *Using Antibodies, Cold Spring Harbor Laboratory Press*, Cold Spring Harbor, N.Y.); Harlow and Lane (1988) *Antibodies A Laboratory Manual*, Cold Spring Harbor Laboratory Press, Cold Spring Harbor, N.Y.; Einhauer, et al. (2001) *J. Biochem. Biophys. Methods* 49:455-465. Methods for adenovirus engineering and transfection, e.g., into cells or mammals, are described (Hurst, et al (2002) *New Engl. J. Med.* 169:443-453; Danthinne and Imperiale (2000) *Gene Ther.* 7:1707-1714; Carlisle (2002) *Curr. Op. Mol. Ther.* 4:306-312.

Methods for protein purification such as immunoprecipitation, column chromatography, electrophoresis, isoelectric focusing, centrifugation, and crystallization, are described (Coligan, et al. (2000) *Current Protocols in Protein Science*, Vol. 1, John Wiley and Sons, Inc., New York). Chemical analysis, chemical modification, post-translational modification, and glycosylation of proteins is described. See, e.g., Coligan, et al. (2000) *Current Protocols in Protein Science*, Vol. 2, John Wiley and Sons, Inc., New York; Walker (ed.) (2002) *Protein Protocols Handbook*, Humana Press, Towota, N.J.; Lundblad (1995) *Techniques in Protein Modification*, CRC Press, Boca Raton, Fla. Techniques for characterizing binding interactions are described (Coligan, et al. (2001) *Current Protocols in Immunology*, Vol. 4, John Wiley and Sons, Inc., New York; Parker, et al. (2000) *J. Biomol. Screen.* 5: 77-88; Karlsson, et al. (1991) *J. Immunol. Methods* 145: 229-240; Neri, et al. (1997) *Nat. Biotechnol.* 15:1271-1275; Jonsson, et al. (1991) *Biotechniques* 11:620-627; Friguet, et al. (1985) *J. Immunol. Methods* 77: 305-319; Hubble (1997) *Immunol. Today* 18:305-306; Shen, et al. (2001) *J. Biol. Chem.* 276:47311-47319).

Computer analysis is performed using software for determining, e.g., antigenic fragments, signal and leader sequences, protein folding, and functional domains, are available, see, e.g., Vector NTI® Suite (Informax, Inc., Bethesda, Md.); GCG Wisconsin Package (Accelrys, Inc., San Diego, Calif.), and DeCypher® (TimeLogic Corp., Crystal Bay, Nev.); Menne, et al. (2000) *Bioinformatics* 16:741-742. Public sequence databases were also used, e.g., from GenBank and others.

II. Wound Generation in p19 Deficient Mice

Mice deficient in the p19 subunit of IL-23 (p19 knockout mice; p19KO mice) were injected with 1 mg of heat killed *Mycobacterium tuberculosis* (strain H37 RA) emulsified in incomplete Freund's adjuvant (IFA) over four dorsal-flank sites. After 14-18 days post exposure to bacterial antigen, the p19KO mice showed significant hair loss and skin lesions. These results suggest that in the absence of IL-23, mice have an abnormal immune response to bacterial antigen challenge leading to an impaired wound healing response.

III. Incision Wound Generation and Assessment of Histological Responses

Incision wounding (5 mm) was performed on the dorsal skin of wild-type (WT) and p19KO mice as described (see, e.g., Cohen and Mast (1990) *Advances in Understanding Trauma and Burn Injury* 30:S149-S155). Eighteen hours after linear incision wounding samples from skin surrounding the incision were harvested and subjected to confocal microscopy. Tissue sections were stained with anti IA-FITC and anti-CD11b-APC. p19KO mice showed delayed recruitment of $CD11b^+$, MHC-class II positive cells, i.e., a delay in the recruitment of bone marrow derived monocytes during the wound healing process.

IL-23 was found to induce recruitment of activated monocytes/macrophages. C57BL/6 mice were injected with 10 micrograms of recombinant IL-23 (rIL-23) at a dorsal intradermal site. Skin samples were stained with anti-IA-FITC and anti-CD11b-APC and analyzed by confocal microscopy. IL-23 induced recruitment of MHC-class $II^+$, $CD11b^+$ monocytes to the site of cytokine injection. PBS treated skin samples appeared negative for recruitment of these monocytes. Taken together, the altered healing response of p19KO mice to injected Mycobacterium tuberculosis and the IL-23 recruitment of activated monocytes/macrophages suggest a role of IL-23 in the wound-healing response.

IL-23 also induced monocyte/macrophage recruitment in wound bed granulation tissue. Ten micrograms of rIL-23 was delivered intradermally to eight sites surrounding two 6 mm full thickness dorsal excisional wounds immediately post-wounding. On day 3, the two wounds and surrounding skin were excised, frozen in OCT, sectioned and stained with anti-CD11b. Counterstaining was done with hematoxyin (blue). IL-23 treated wound tissue exhibited higher monocyte/macrophage infiltrate than buffer control 3 days post-wounding. Similar results were found for $CD31^+$ endothelial cell migration.

Recombinant IL-23 was found to augment wound healing. Ten micrograms of rIL-23 was delivered intradermally to eight sites surrounding 6 mm full thickness excisional wounds on the backs of healing competent wild-type Balb/c mice immediately post wounding. On day 3 post wounding the two excisional wounds plus additional surrounding skin were excised. Wounds were fixed in formaldehyde, paraffin embedded and stained with hematoxylin and eosin. Histology slides were assessed for the depth of granulation tissue. IL-23 treated mice exhibited a greater thickness of the granulation tissue layer as compared to buffer control treated mice. Increase in the granulation tissue layer is imperative for late stage wound healing (see, e.g., Schaffer and Nanney, supra). Similar results were at 3, 6, and 10 days post wounding.

The same procedure was utilized to determine if IL-23 augments the normal re-epithelialization that occurs in wound healing. IL-23 treated mice exhibited thicker keratinocyte layers than buffer control mice.

IV. Incision Wound Healing and Assessment of Breaking Strength

Twelve week old male C57Bl/6NT mice were shaved and hair was removed from the dorsum using a depilatory (Nair®, Church and Dwight Co., Princeton, N.J.). Two 0.5 cm incisional wounds were created approximately 4 cm down from the nape of the neck and 1 cm away from the midline using surgical scissors. Each mouse received four 20 microliter intradermal injections with either saline or mIL-23 (10 micrograms per mouse) around the periphery of each wound to span the entire length of the incision on both sides. Each wound was closed using a medical adhesive (Mastisol®, Ferndale Labs., Femdale, Mich.) and transparent dressing (OpSite 3000®, Smith and Nephew, Largo, Fla.). Three days later, mice were anesthetized with a ketamine/xylazine cocktail and wounds were analyzed in vivo using a biomechanical tissue characterizer (BTC-2000, SRLI Technologies, Nashville, Tenn.), according to manufacturer's instructions. The BTC-2000 uses a high resolution target laser and vacuum to measure skin deformation over a range of negative pressure and time. Negative pressure was applied at a rate of 10 mm Hg/second until wound rupture occurred.

Data were analyzed by plotting skin deformation as a function of negative pressure to give: 1) the stiffness of the healing wound (mmHg negative pressure required to deform the tissue) and 2) the total strength of the healing wound (i.e. mmHg negative pressure required to break the wound). Tests comparing saline-treated controls with mIL-23-treated experimentals demonstrated that 46% more negative pressure was required to break mIL-23-treated wounds (195.6 mm Hg) than to break to saline-treated wounds (134.1 mm Hg). Moreover, the healing wound following mIL-23 treatment (262.7 mm Hg/mm) was stiffer in comparison to saline-treated controls (198.4 mm Hg/mm).

Administration of an IL-23 agonist is contemplated to result in a desirable increase in stiffness (or reduction in looseness) of the healed wound, beyond which, an undesirable increase in stiffness (or undesirable reduction of looseness) occurs. Hence, an IL-23 antagonist is provided for reducing any undesirable stiffness (or undesired reduction of looseness) of a naturally healing wound or an IL-23 agonist treated wound. Alternatively, for example, an IL-23 agonist is contemplated to result in a decrease in undesirable stiffness, e.g., due to excess fibrosis. Hence, an IL-23 agonist is provided to reduce any undesirable stiffness.

V. IL-23 Treatment Increases Granulation Tissue

The wound healing response in the mouse back excisional model is mediated by the combination of increased granulation tissue formation, re-epithelialization, and wound contraction. One phase of wound contraction in this model occurs very early and contributes significantly to the overall wound closure. To confirm that IL-23 wound healing promotion activities were also seen in a mouse model that did not have a prominent early wound contraction aspect to the healing response, the mouse head excisional model was chosen.

10 micrograms of recombinant IL-23 was delivered intradermally to 4 sites surrounding one 3 mm full thickness excisional wound on the crown of Balb/c mice's heads immediately post-wounding. On Day 3 post-wounding, the wound and surrounding skin were excised. Wounds were fixed in formaldehyde, paraffin embedded, and stained with hematoxylin and esoin (H/E). Histology slides from the center of the wound were assessed for the depth of granulation tissue.

The data at day 3 post wound infliction indicates that the increased granulation tissue activity resulting from IL-23 treatment was seen prior to the start of later-stage contraction and therefore is independent of early phase wound contraction. Note that a later-wound contraction phase also occurs in this model, but this occurs only after day 4-6.

VI. Gene Therapy

IL-23 is delivered to the site of a cutaneous wound using gene therapy technology. Therapeutic delivery to the skin is accomplished by ex vivo or in vivo methods (see, e.g., Khavari (1997) *Mol. Med. Today* 3:533-538 and Khavari, et al. (2002) *J. Int. Med.* 252:1-10).

Recombinant adenoviral preparation were prepared by conventional techniques, see, e.g., Srivastava in WO 93/09239, Samulski et al. (1989) *J. Virol.* 63:3822-3828; Mendelson et al. (1988) *Virol.* 166:154-165; and Flotte et al. (1993) *Proc. Natl. Acad. Sci. USA* 90:10613-10617). Increasing number of adenoviral particles encoding mouse IL-23 hyperkine or green fluorescent protein (GFP) or saline diluent were delivered intradermally to 8 sites surrounding two 6 mm full thickness excisional wounds on the backs of Balb/c mice immediately post-wounding. On Day 3 post-wounding, the two wounds and surrounding skin were excised. Wounds were fixed in formaldehyde, paraffin embedded, and stained with hematoxylin and esoin (H/E). Histology slides from the center of the wound were assessed for the depth of granulation tissue. Delivery of mIL-23 hyperkine by this method resulted in an increased wound healing response as compared to vehicle alone.

VII. Gene Expression with mIL-23 Hyperkine Treatment

Excisional wounds were created on the backs of C57Bl6/NT mice. Wounds were treated with 10 micrograms of mIL-23 hyperkine or saline control by intradermal (i.d.) injection around the periphery of the wound. Wounds were harvested at Day 1 and at Day 3 post-wounding. Skin samples distal to the wounded site were obtained as "non-wounded" controls. Taqman® real time PCR analysis (Applied Biosystems, Foster City, Calif.) was performed on the tissue samples. Expression data were relative to ubiquitin expression, where ubiquitin expression was set to one (1.0). Expression data were then compared according to the indicated pairs of data sets.

Expression was examined with and without IL-23 hyperkine treatment, in the absence of wounding (Table 1) and with and without IL-23 hyperkine with wounding (Table 2). C57Bl6/NT mice were treated with IL-23 hyperkine or saline, followed by determination of expression of the indicated gene by Taqman® real time PCR analysis (Table 1). Each mouse was injected intradermally, in the back, with either saline or with 10 micrograms IL-23 hyperkine. Tissue samples were taken and extracted at either 1, 3, or 7 days after injection, where the samples from the three dates were pooled, and then used for Taqman® analysis. The ratio of gene expression with and without IL-23 hyperkine treatment is shown (Table 1). IL-23 hyperkine provoked an increase in expression, of 2-fold or greater, of 15 of the 157 genes tested. These included IL-6 (33-fold), IL-19 (32-fold), and CXCL-1 (GRO-alpha) (11-fold) (Table 1).

TABLE 1

Ratio of [Gene expression with IL-23]/[Gene expression with saline]. Control (saline) and experimental (IL-23) data were acquired without wounding.

| | |
|---|---|
| IL-6 | 33 |
| IL-19 | 32 |
| CXCL-1 (GRO-alpha) | 11 |
| IL-17 | 9 |
| mMUC-5ac.fcgi | 8 |
| secretory leukoprotease inhibitor (SLPI) | 5 |

TABLE 1-continued

Ratio of [Gene expression with IL-23]/[Gene expression with saline].
Control (saline) and experimental (IL-23) data were acquired
without wounding.

| | |
|---|---|
| granulocyte macrophage-colony stimulating factor (GM-CSF) | 5 |
| TNFSF5 (CD40L) | 3 |
| MAdCAM-1 | 3 |
| interferon-gamma (IFN-gamma) | 3 |
| IL-9 | 3 |
| 12-lipoxygenase | 2 |
| tissue inhibitor of metalloproteinases-1 (TIMP-1) | 2 |
| IL-1alpha | 2 |
| IL-17RC | 2 |

Expression data from Day 1 (1 day after wounding) and from Day 3 (3 days after wounding) are shown (Table 2). IL-23 with wounding stimulated increases in expression over that found with wounding only for a number of genes associated with healing or neutrophil response, including IL-17, nitric oxide synthase, lactoferrin, and matrix metalloproteases (Table

TABLE 2

Ratio of [Gene expression with IL-23, with wound]/[Gene
expression with saline, with wound]

| | Day 1 | Day 3 |
|---|---|---|
| IL-17 | 234 | 6.7 |
| nitric oxide synthase 2 (NOS2) | 17 | — |
| lactoferrin | 5.3 | 8.9 |
| IL-12 (p35 subunit) | 3.9 | — |
| IL-12 (p40 subunit) | 3.6 | — |
| CD107 (LAMP-2; mac-3) | 3.5 | — |
| integrin beta7 chain | 3.4 | — |
| TNFSF11 (RANKL) | 3.3 | — |
| CD11a (LFA-1a chain) | 3.0 | — |
| IL-19 | 2.9 | 2.0 |
| endoperoxidase synthase type II (COX-2) | 2.8 | — |
| IL-1RA | 2.8 | — |
| IL-17RA | 2.7 | — |
| CD29 (integrin b1) | 2.6 | — |
| leukotriene A4 hydrolase | 2.5 | — |
| MMP-13 | 2.4 | — |
| MMP-8 (collagenase 2) | 2.4 | — |
| leukotriene B4 receptor | 2.4 | — |
| TNFRSF11a (RANK) | 2.4 | — |
| M-CSF1 | 2.3 | — |
| TIMP-1 | 2.3 | — |
| CD14 | 2.3 | — |
| TNF-alpha converting enzyme (TACE) | 2.3 | — |
| Mac-1 alpha subunit (CD11b) | 2.3 | — |
| DEC-205 | 2.2 | — |
| CD50 (ICAM-1) | 2.2 | — |
| CCL3 MIP-1alpha | 2.2 | — |
| CD86 (B7-2) | 2.2 | — |
| CD80 (B7-1) | 2.1 | — |
| IL-80 | 2.1 | — |
| fibronectin | 2.0 | — |
| TNFRSF6a (FAS) | 2.0 | — |
| neutrophil elastase | 0.1 | 13.7 |
| interferon-gamma (IFN-gamma) | 0.7 | 8.7 |
| matrilysin (MMP-7) | 0.1 | 5.3 |
| TNFRSF7u (CD27) | 0.8 | 4.9 |
| IL-13Ra2 | 1.4 | 4.8 |
| IL-12Rb1 | 1.6 | 3.8 |
| myeloperoxidase | 1.1 | 2.7 |
| eosinophil major basic protein | 0.4 | 2.7 |
| proteinase 3 | 1.6 | 2.6 |
| IL-15 | 1.4 | 2.5 |

IL-23 dependent trends in gene expression in common with two strains of mice (C57B1/6NT mice; Balb/c mice) were as follows. A panel of 158 genes was screened to determine which are regulated by IL-23 treatment during wound healing. Only five of these genes were upregulated by at least 2-fold (Table 3), and only three of the genes were down regulated by 2-fold or greater (Table 3).

IL-17 has been shown to regulate genes important for remodeling in other tissue systems. IL-17 potentiates both MMP-3 and TIMP-1 expression and secretion stimulated by TNF and IL-1 in human colonic subepithelial myofibroblasts (Bamba, et al. (2003) *J Gastroenterol.* 38:548-554). In human osteoblasts, IL-17 synergizes with TNF-alpha, TGF-beta, and IFN-gamma to stimulate production of MMP-13 (Rifas and Arackal (2003) *Arthritis Rheum.* 48:993-1001). Given that IL-17 alone has minimal effects in these models, the major role of IL-17 may be to amplify the remodeling response. IL-19 is found in skin and has been associated with psoriasis (Ghoreschik, et al. (2003) *Nature Med.* 9:40-46; Gallagher, et al. (2000) *Genes Immunity* 1:442-450). Lactoferrin is an iron-binding protein present in mature neutrophil granules with a number of biological functions including anti-microbial properties and may thus protect against bacterial infection in the wound (Masson, et al. (1969) *J. Exp. Med.* 130:643-658; Farnaud and Evans (2003) *Mol Immunol.* 40:395-405). ICAM-2 is constitutively expressed on all vascular endothelial cells suggesting that IL-23 may promote angiogenesis in the wound (Yasuda, et al. (2002) *Am. J. Physiol.* 282:C917-C925; Sakurai, et al. (2003) *Invest. Ophthalmol. Vis. Sci.* 44:2743-2749; Moromizato, et al. (2000) *Am. J. Pathol.* 157: 1277-1281). DEC-205 is a dendritic cell marker implicated in the dendritic cell maturation (Anjuere, et al. (1999) *Blood* 93:590-598; Bonifax, et al. (2002) *J. Exp. Med.* 196:1627-1638). Thus IL-23 of the present invention can promote immune surveillance in the skin.

Taken together, IL-23 treatment in wounds may have pleiotropic effects to accelerate the wound healing response. IL-23 treatment also reduced the expression of 3 genes in the wound environment, i.e., IL-25, TNSF7, and eosinophilic basic protein. Infusion of mice with IL-25 induced IL-4, IL-5, and IL-13 gene expression associated with lung remodeling pathology (Fort, et al. (2001) *Immunity* 15:985-995). Thus, IL-23 may modulate or reduce excess fibrosis in wound healing.

Relevant methodology was as follows. Hair was shaved and removed with Nair from the dorsum of 9 week old male C57B1/6NT and 8 week old male Balb/c mice. Two 6 mm diameter excisional wounds were created approximately 3.5 cm down from the nape of the neck and 0.6 cm away from the midline using a punch biopsy tool. Each mouse was given mIL-23 hyperkine (10 micrograms per mouse) or saline in four 20 microliters intradermal injections around the periphery of each wound. A transparent dressing was applied and mice were allowed to recover and heal. One day later, mice were sacrificed and wounds were excised with a margin of approximately 1.5 mm. In addition, a sample of non-wounded skin from each mouse was obtained. All samples were snap frozen in liquid nitrogen and stored at −80 degrees Celsius for further processing. RNA was extracted from each sample, pooled together into appropriate groups, and analyzed by real time PCR for expression of a panel of 158 candidate genes.

TABLE 3

Modulation of gene expression, by at least 2-fold, in response to IL-23 in both C57B1/6NT mice and Balb/c mice.

|  | C57B1/6NT mouse | Balb/c mouse |
|---|---|---|
| Genes up-regulated. | | |
| IL-17 | 234.5 | 207.9 |
| Lactoferrin | 5.3 | 3.3 |
| IL-19 | 2.9 | 2.2 |
| DEC-205 | 2.3 | 2.8 |
| CD50 (ICAM-2) | 2.3 | 2.1 |
| Genes down-regulated. | | |
| IL-25 | 5.88 | 5.56 |
| TNSF7-CD27L | 3.45 | 100 |
| Eosinophilic basic protein | 2.13 | 2.33 |

VIII. Agonist Anti-IL-23R Antibodies

Mouse anti-IL-23R antibodies were prepared against human IL-23R using standard methods. The resultant anti-IL-23R antibodies were screened for agonist activity using cells transfected with hIL-23R and hIL-12Rbeta1, where agonist activity was determined by increases in cell proliferation. Proliferation of transfectant Ba/F3 cells was measured by calorimetric methods using Alamar Blue, a growth indicator dye.

Cell proliferation was measured after culture in Roswell Park Memorial Institute (RPMI)-1640 medium, fetal calf serum (10%), 0.05 mM 2-mercaptoethanol, glutamine, penicillin, streptomycin, and mouse interleukin-3 (mIL-3) (10 ng/ml). Cells were incubated in the presence of one concentration of antibody, where the concentrations ranged from 0.01 to 10,000 ng/ml. Baseline cell proliferation was that in absence of antibody. Maximal proliferation with the antibodies tested occurred in the concentration range of 1000 to 10,000 ng/ml. "Detectable stimulation," e.g., of cell activity, cell proliferation, or a predetermined activity, refers, e.g., to a comparison of proliferation in the presence and absence of, e.g., an IL-23 agonist. "Detectable" may be a function of the context, e.g., of the reagents, instrumentation, or biological system.

Antibodies that stimulated expression included TC48-8B10.D5 (light chain, SEQ ID NOs:9 and 10; heavy chain, SEQ ID NOs:11 and 12), TC48-1H3.G5, TC48-2C9A5, and TC48-5B12.C9. Of these antibodies, TC48-8B10.D5 showed the greatest agonist activity, in terms of antibody concentration provoking ½ maximal increase in cell proliferation. 100% cell proliferation means maximal increase in cell proliferation in response to the antibody, in titration curves (Table 4). The predicted cleavage point for the signal sequence of the light chain of TC48-8B10.D5 is between amino acids 22 (Ala) and 23 (Glu) of SEQ ID NO:10, while the predicted cleavage point for the heavy chain is between amino acids 19 (Ser) and 20 (Gln) of SEQ ID NO:12.

TABLE 4

Proliferation of Ba/F3-2.2lo cells in response to agonistic antibodies.

| Antibody | Maximal increase cell proliferation in response to antibody (units of $OD_{570-600\,nm}$) | Antibody concentration providing ½ maximal increase in cell proliferation. |
|---|---|---|
| TC48-8B10.D5 (SEQ ID NOs: 9-12) | 0.026 | 10 ng/ml |
| TC48-2C9A5 | 0.021 | 20 ng/ml |
| TC48-1H3.G5 | 0.018 | 50 ng/ml |
| TC48-5B12.C9 | 0.026 | 100 ng/ml |

The invention provides an agonistic murine antibody that specifically binds human IL-23R, TC48-8B10.D5. This antibody comprises a nucleic acid (SEQ ID NO:9) and polypeptide (SEQ ID NO:10) of the light chain, and the nucleic acid (SEQ ID NO:11) and polypeptide (SEQ ID NO:12) of the heavy chain of TC48-8B10.D5. Also provided are the nucleic acids and polypeptides comprising the hypervariable regions of SEQ ID NOs:9-12. The hypervariable regions of the light chain are: ITSTDIDDDMI (amino acids 46-56); EGNTLRP (amino acids 72-78); and LQSDNMPLT (amino acids 111-119), of SEQ ID NO:10. The hypervariable regions of the heavy chain are: GYTFTSYWMN (amino acids 45-54); MIDPLDSETHYNQMFKD (amino acids 69-87); and GDNYYAMDY (amino acids 118-126), of SEQ ID NO:12.

IX. Rat Anti-Mouse IL-23R Antibodies and Wound Healing

Antibodies against mouse IL-23R were raised in rats using standard methods, resulting in antibodies named 5C10, 29A5, and 10E11 (Table 5). An IL-23 hyperkine comprising a p19 subunit and p40 subunit covalently connected by way of an elasti-linker (InvivoGen, San Diego, Calif.) was prepared, and named "IL-23 elastikine." The anti-mouse IL-23R antibodies, IL-23 elastikine (control), 36E10 antibody (isotype control), and saline (control) were tested in a wound healing assay. The results demonstrated a stimulation of wound healing with the IL-23 elastikine, and lesser stimulation with the 5C10 antibody (Table 5.)

TABLE 5

Wound healing; thickness of granulation tissue (micrometers).

| Saline control | 170 micrometers |
|---|---|
| IL-23 elastikine control | 300 |
| 36E10 isotype control | 170 |
| 5C10 | 205 |
| 29A5 | 170 |
| 10E11 | 125 |

The sequences in the Sequence Listing are summarized (Table 6).

TABLE 6

Sequences in Sequence Listing.

| SEQ ID NO: | Nucleic acid or Polypeptide |
|---|---|
| 1 | Mouse IL-19 nucleic acid |
| 2 | Mouse IL-19 polypeptide |
| 3 | Human IL-19 nucleic acid |
| 4 | Human IL-19 polypeptide |
| 5 | Mouse hyperkine nucleic acid |

TABLE 6-continued

Sequences in Sequence Listing.

| SEQ ID NO: | Nucleic acid or Polypeptide |
|---|---|
| 6 | Mouse hyperkine polypeptide |
| 7 | Human hyperkine nucleic acid |
| 8 | Human hyperkine polypeptide |
| 9 | Mouse anti-human agonist Ab light chain nucleic acid |
| 10 | Mouse anti-human agonist Ab light chain polypeptide |
| 11 | Mouse anti-human agonist Ab heavy chain nucleic acid |
| 12 | Mouse anti-human agonist Ab heavy chain polypeptide |

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated agonist antibody, or antigen binding fragment thereof, that specifically binds to human IL-23 receptor (hIL-23R), wherein contact of the agonist antibody to a cell expressing hIL-23R and hIL-12Rβ1 results in an increase in proliferation of the cell.

2. The agonist antibody, or antigen-binding fragment thereof, of claim 1 that is a monoclonal antibody or antigen-binding fragment thereof.

3. The agonist antibody, or antigen-binding fragment thereof, of claim 2 that is a Fab, Fv, or F(ab')₂ fragment.

4. The agonist antibody, or antigen-binding fragment thereof, of claim 1, comprising:

a) a light chain comprising the mature amino acid sequence of SEQ ID NO:10; and
b) a heavy chain comprising the mature amino acid sequence of SEQ ID NO:12.

5. The agonist antibody, or antigen-binding fragment thereof, of claim 1, comprising two light chains and two heavy chains.

6. The agonist antibody, or antigen-binding fragment thereof, of claim 1 that is a humanized antibody or antigen-binding fragment thereof.

7. The agonist antibody, or antigen-binding fragment thereof, of claim 6 that is a Fab, Fv, or F(ab')$_2$ fragment.

8. The agonist antibody, or antigen-binding fragment thereof, of claim 1, comprising:
 a) a light chain comprising hypervariable regions consisting of:
  i) a first CDR consisting of residues 46-56 of SEQ ID NO: 10;
  ii) a second CDR consisting of residues 72-78 of SEQ ID NO: 10; and
  iii) a third CDR consisting of residues 111-119 of SEQ ID NO: 10;
 and
 b) a heavy chain comprising hypervariable regions consisting of:
  i) a first CDR consisting of residues 45-54 of SEQ ID NO: 12;
  ii) a second CDR consisting of residues 69-87 of SEQ ID NO: 12; and
  iii) a third CDR consisting of residues 118-126 of SEQ ID NO: 12.

* * * * *

```
SEQUENCE LISTING

<160> NUMBER OF SEQ ID NOS: 12

<210> SEQ ID NO 1
<211> LENGTH: 1203
<212> TYPE: DNA
<213> ORGANISM: Mus musculus
<220> FEATURE:
<221> NAME/KEY: CDS
<222> LOCATION: (113)..(700)
<220> FEATURE:
<221> NAME/KEY: mat_peptide
<222> LOCATION: (176)..(700)

<400> SEQUENCE: 1
cgcttagaag tcggactaca gagttagact cagaaccaaa ggaggtggat aggggggtcca         60 caggcctggt gcagatcaca gagccagcca gatctgagaa gcagggaaca ag atg ctg        118
                                                          Met Leu
                                                          -20 gat tgc aga gca gta ata atg cta tgg ctg ttg ccc tgg gtc act cag          166
Asp Cys Arg Ala Val Ile Met Leu Trp Leu Leu Pro Trp Val Thr Gln
             -15                 -10                  -5 ggc ctg gct gtg cct agg agt agc agt cct gac tgg gct cag tgc cag          214
Gly Leu Ala Val Pro Arg Ser Ser Ser Pro Asp Trp Ala Gln Cys Gln
    -1   1                   5                   10 cag ctc tct cgg aat ctc tgc atg cta gcc tgg aac gca cat gca cca          262
Gln Leu Ser Arg Asn Leu Cys Met Leu Ala Trp Asn Ala His Ala Pro
         15                  20                  25 gcg gga cat atg aat cta cta aga gaa gaa gag gat gaa gag act aaa          310
Ala Gly His Met Asn Leu Leu Arg Glu Glu Glu Asp Glu Glu Thr Lys
 30                  35                  40                  45 aat aat gtg ccc cgt atc cag tgt gaa gat ggt tgt gac cca caa gga          358
Asn Asn Val Pro Arg Ile Gln Cys Glu Asp Gly Cys Asp Pro Gln Gly
                 50                  55                  60 ctc aag gac aac agc cag ttc tgc ttg caa agg atc cgc caa ggt ctg          406
Leu Lys Asp Asn Ser Gln Phe Cys Leu Gln Arg Ile Arg Gln Gly Leu
             65                  70                  75 gct ttt tat aag cac ctg ctt gac tct gac atc ttc aaa ggg gag cct          454
Ala Phe Tyr Lys His Leu Leu Asp Ser Asp Ile Phe Lys Gly Glu Pro
         80                  85                  90 gct cta ctc cct gat agc ccc atg gag caa ctt cac acc tcc cta cta          502
Ala Leu Leu Pro Asp Ser Pro Met Glu Gln Leu His Thr Ser Leu Leu
     95                 100                 105 gga ctc agc caa ctc ctc cag cca gag gat cac ccc cgg gag acc caa          550
Gly Leu Ser Gln Leu Leu Gln Pro Glu Asp His Pro Arg Glu Thr Gln
110                 115                 120                 125 cag atg ccc agc ctg agt tct agt cag cag tgg cag cgc ccc ctt ctc          598
```

```
Gln Met Pro Ser Leu Ser Ser Gln Gln Trp Gln Arg Pro Leu Leu
        130                 135                 140 cgt tcc aag atc ctt cga agc ctc cag gcc ttt ttg gcc ata gct gcc     646
Arg Ser Lys Ile Leu Arg Ser Leu Gln Ala Phe Leu Ala Ile Ala Ala
            145                 150                 155 cgg gtc ttt gcc cac gga gca gca act ctg act gag ccc tta gtg cca     694
Arg Val Phe Ala His Gly Ala Ala Thr Leu Thr Glu Pro Leu Val Pro
        160                 165                 170 aca gct taaggatgcc caggttccca tggctaccat gataagacta atctatcagc      750
Thr Ala
    175 ccagacatct accagttaat taacccatta ggacttgtgc tgttcttgtt tcgtttgttt    810 tgcgtgaagg gcaaggacac cattattaaa gagaaaagaa acaaaccccca gagcaggcag   870 ctggctagag aaaggagctg gagaagaaga ataaagtctc gagcccttgg ccttggaagc    930 gggcaagcag ctgcgtggcc tgaggggaag ggggcggtgg catcgagaaa ctgtgagaaa    990 acccagagca tcagaaaaag tgagcccagg ctttggccat tatctgtaag aaaaacaaga   1050 aaagggaac attatacttt cctgggtggc tcagggaaat gtgcagatgc acagtactcc    1110 agacagcagc tctgtacctg cctgctctgt ccctcagttc taacagaatc tagtcactaa   1170 gaactaacag gactaccaat acgaactgac aaa                                1203

<210> SEQ ID NO 2
<211> LENGTH: 196
<212> TYPE: PRT
<213> ORGANISM: Mus musculus

<400> SEQUENCE: 2

Met Leu Asp Cys Arg Ala Val Ile Met Leu Trp Leu Leu Pro Trp Val
    -20                 -15                 -10

Thr Gln Gly Leu Ala Val Pro Arg Ser Ser Ser Pro Asp Trp Ala Gln
 -5                  -1   1               5                  10

Cys Gln Gln Leu Ser Arg Asn Leu Cys Met Leu Ala Trp Asn Ala His
                15                  20                  25

Ala Pro Ala Gly His Met Asn Leu Leu Arg Glu Glu Asp Glu Glu
            30                  35                  40

Thr Lys Asn Asn Val Pro Arg Ile Gln Cys Glu Asp Gly Cys Asp Pro
        45                  50                  55

Gln Gly Leu Lys Asp Asn Ser Gln Phe Cys Leu Gln Arg Ile Arg Gln
 60                  65                  70                  75

Gly Leu Ala Phe Tyr Lys His Leu Leu Asp Ser Asp Ile Phe Lys Gly
                80                  85                  90

Glu Pro Ala Leu Leu Pro Asp Ser Pro Met Gln Leu His Thr Ser
            95                 100                 105

Leu Leu Gly Leu Ser Gln Leu Leu Gln Pro Glu Asp His Pro Arg Glu
        110                 115                 120

Thr Gln Gln Met Pro Ser Leu Ser Ser Gln Gln Trp Gln Arg Pro
125                 130                 135

Leu Leu Arg Ser Lys Ile Leu Arg Ser Leu Gln Ala Phe Leu Ala Ile
140                 145                 150                 155

Ala Ala Arg Val Phe Ala His Gly Ala Ala Thr Leu Thr Glu Pro Leu
                160                 165                 170

Val Pro Thr Ala
            175
```

```
<210> SEQ ID NO 3
<211> LENGTH: 570
<212> TYPE: DNA
<213> ORGANISM: Homo sapiens
<220> FEATURE:
<221> NAME/KEY: CDS
<222> LOCATION: (1)..(567)
<220> FEATURE:
<221> NAME/KEY: mat_peptide
<222> LOCATION: (64)..(567)

<400> SEQUENCE: 3 atg ctg ggg agc aga gct gta atg ctg ctg ttg ctg ctg ccc tgg aca      48
Met Leu Gly Ser Arg Ala Val Met Leu Leu Leu Leu Leu Pro Trp Thr
    -20                 -15                 -10 gct cag ggc aga gct gtg cct ggg ggc agc agc cct gcc tgg act cag      96
Ala Gln Gly Arg Ala Val Pro Gly Gly Ser Ser Pro Ala Trp Thr Gln
 -5              -1   1               5                  10 tgc cag cag ctt tca cag aag ctc tgc aca ctg gcc tgg agt gca cat     144
Cys Gln Gln Leu Ser Gln Lys Leu Cys Thr Leu Ala Trp Ser Ala His
             15                  20                  25 cca cta gtg gga cac atg gat cta aga gaa gag gga gat gaa gag act     192
Pro Leu Val Gly His Met Asp Leu Arg Glu Glu Gly Asp Glu Glu Thr
         30                  35                  40 aca aat gat gtt ccc cat atc cag tgt gga gat ggc tgt gac ccc caa     240
Thr Asn Asp Val Pro His Ile Gln Cys Gly Asp Gly Cys Asp Pro Gln
     45                  50                  55 gga ctc agg gac aac agt cag ttc tgc ttg caa agg atc cac cag ggt     288
Gly Leu Arg Asp Asn Ser Gln Phe Cys Leu Gln Arg Ile His Gln Gly
60                  65                  70                  75 ctg att ttt tat gag aag ctg cta gga tcg gat att ttc aca ggg gag     336
Leu Ile Phe Tyr Glu Lys Leu Leu Gly Ser Asp Ile Phe Thr Gly Glu
                 80                  85                  90 cct tct ctg ctc cct gat agc cct gtg gcg cag ctt cat gcc tcc cta     384
Pro Ser Leu Leu Pro Asp Ser Pro Val Ala Gln Leu His Ala Ser Leu
             95                 100                 105 ctg ggc ctc agc caa ctc ctg cag cct gag ggt cac cac tgg gag act     432
Leu Gly Leu Ser Gln Leu Leu Gln Pro Glu Gly His His Trp Glu Thr
        110                 115                 120 cag cag att cca agc ctc agt ccc agc cag cca tgg cag cgt ctc ctt     480
Gln Gln Ile Pro Ser Leu Ser Pro Ser Gln Pro Trp Gln Arg Leu Leu
    125                 130                 135 ctc cgc ttc aaa atc ctt cgc agc ctc cag gcc ttt gtg gct gta gcc     528
Leu Arg Phe Lys Ile Leu Arg Ser Leu Gln Ala Phe Val Ala Val Ala
140                 145                 150                 155 gcc cgg gtc ttt gcc cat gga gca gca acc ctg agt ccc taa             570
Ala Arg Val Phe Ala His Gly Ala Ala Thr Leu Ser Pro
                160                 165

<210> SEQ ID NO 4
<211> LENGTH: 189
<212> TYPE: PRT
<213> ORGANISM: Homo sapiens

<400> SEQUENCE: 4

Met Leu Gly Ser Arg Ala Val Met Leu Leu Leu Leu Leu Pro Trp Thr
    -20                 -15                 -10

Ala Gln Gly Arg Ala Val Pro Gly Gly Ser Ser Pro Ala Trp Thr Gln
 -5              -1   1               5                  10

Cys Gln Gln Leu Ser Gln Lys Leu Cys Thr Leu Ala Trp Ser Ala His
             15                  20                  25

Pro Leu Val Gly His Met Asp Leu Arg Glu Glu Gly Asp Glu Glu Thr
```

-continued

```
                30                  35                  40
Thr Asn Asp Val Pro His Ile Gln Cys Gly Asp Gly Cys Asp Pro Gln
             45                  50                  55

Gly Leu Arg Asp Asn Ser Gln Phe Cys Leu Gln Arg Ile His Gln Gly
 60                  65                  70                  75

Leu Ile Phe Tyr Glu Lys Leu Leu Gly Ser Asp Ile Phe Thr Gly Glu
                 80                  85                  90

Pro Ser Leu Leu Pro Asp Ser Pro Val Ala Gln Leu His Ala Ser Leu
                 95                 100                 105

Leu Gly Leu Ser Gln Leu Leu Gln Pro Glu Gly His His Trp Glu Thr
            110                 115                 120

Gln Gln Ile Pro Ser Leu Ser Pro Ser Gln Pro Trp Gln Arg Leu Leu
        125                 130                 135

Leu Arg Phe Lys Ile Leu Arg Ser Leu Gln Ala Phe Val Ala Val Ala
140                 145                 150                 155

Ala Arg Val Phe Ala His Gly Ala Ala Thr Leu Ser Pro
                160                 165
```

```
<210> SEQ ID NO 5
<211> LENGTH: 1610
<212> TYPE: DNA
<213> ORGANISM: Mus musculus
<220> FEATURE:
<221> NAME/KEY: CDS
<222> LOCATION: (7)..(1599)

<400> SEQUENCE: 5
```

| | | | | | | | | | | | | | |
|---|---|---|---|---|---|---|---|---|---|---|---|---|---|
| agatct | atg | tct | gca | ctt | ctg | atc | cta | gct | ctt | gtt | gga | gct gca gtt | 48 |
| | Met | Ser | Ala | Leu | Leu | Ile | Leu | Ala | Leu | Val | Gly | Ala Ala Val | |
| | 1 | | | | 5 | | | | | 10 | | | |

```
gct gac tac aaa gac gat gac gac aag ctt atg tgg gag ctg gag aaa    96
Ala Asp Tyr Lys Asp Asp Asp Asp Lys Leu Met Trp Glu Leu Glu Lys
 15                  20                  25                  30 gac gtt tat gtt gta gag gtg gac tgg act ccc gat gcc cct gga gaa   144
Asp Val Tyr Val Val Glu Val Asp Trp Thr Pro Asp Ala Pro Gly Glu
                 35                  40                  45 aca gtg aac ctc acc tgt gac acg cct gaa gaa gat gac atc acc tgg   192
Thr Val Asn Leu Thr Cys Asp Thr Pro Glu Glu Asp Asp Ile Thr Trp
             50                  55                  60 acc tca gac cag aga cat gga gtc ata ggc tct gga aag acc ctg acc   240
Thr Ser Asp Gln Arg His Gly Val Ile Gly Ser Gly Lys Thr Leu Thr
 65                  70                  75 atc act gtc aaa gag ttt ctr gat gct ggc cag tac acc tgc cac aaa   288
Ile Thr Val Lys Glu Phe Xaa Asp Ala Gly Gln Tyr Thr Cys His Lys
             80                  85                  90 gga ggc gag act ctg agc cac tca cat ctg ctg ctc cac aag aag gaa   336
Gly Gly Glu Thr Leu Ser His Ser His Leu Leu Leu His Lys Lys Glu
 95                 100                 105                 110 aat gga att tgg tcc act gaa att tta aaa aat ttc aaa aac aag act   384
Asn Gly Ile Trp Ser Thr Glu Ile Leu Lys Asn Phe Lys Asn Lys Thr
                115                 120                 125 ttc ctg aag tgt gaa gca cca aat tac tcc gga cgg ttc acg tgc tca   432
Phe Leu Lys Cys Glu Ala Pro Asn Tyr Ser Gly Arg Phe Thr Cys Ser
            130                 135                 140 tgg ctg gtg caa aga aac atg gac ttg aag ttc aac atc aag agc agt   480
Trp Leu Val Gln Arg Asn Met Asp Leu Lys Phe Asn Ile Lys Ser Ser
        145                 150                 155 agc agt tcc cct gac tct cgg gca gtg aca tgt gga atg gcg tct ctg   528
Ser Ser Ser Pro Asp Ser Arg Ala Val Thr Cys Gly Met Ala Ser Leu
```

-continued

```
            160                 165                 170
tct gca gag aag gtc aca ctg gac caa agg gac tat gag aag tat tca    576
Ser Ala Glu Lys Val Thr Leu Asp Gln Arg Asp Tyr Glu Lys Tyr Ser
175                 180                 185                 190 gtg tcc tgc cag gag gat gtc acc tgc cca act gct gag gag acc ctg    624
Val Ser Cys Gln Glu Asp Val Thr Cys Pro Thr Ala Glu Glu Thr Leu
                195                 200                 205 ccc att gaa ctg gcg ttg gaa gca cgg cag cag aat aaa tat gag aac    672
Pro Ile Glu Leu Ala Leu Glu Ala Arg Gln Gln Asn Lys Tyr Glu Asn
            210                 215                 220 tac agc acc agc ttc ttc atc agg gac atc atc aaa cca gac ccg ccc    720
Tyr Ser Thr Ser Phe Phe Ile Arg Asp Ile Ile Lys Pro Asp Pro Pro
            225                 230                 235 aag aac ttg cag atg aag cct ttg aag aac tca cag gtg gag gtc agc    768
Lys Asn Leu Gln Met Lys Pro Leu Lys Asn Ser Gln Val Glu Val Ser
            240                 245                 250 tgg gag tac cct gac tcc tgg agc act ccc cat tcc tac ttc tcc ctc    816
Trp Glu Tyr Pro Asp Ser Trp Ser Thr Pro His Ser Tyr Phe Ser Leu
255                 260                 265                 270 aag ttc ttt gtt cga atc cag cgc aag aaa gaa aag atg aag gag aca    864
Lys Phe Phe Val Arg Ile Gln Arg Lys Lys Glu Lys Met Lys Glu Thr
                275                 280                 285 gag gag ggg tgt aac cag aaa ggt gcg ttc ctc gta gag aag aca tct    912
Glu Glu Gly Cys Asn Gln Lys Gly Ala Phe Leu Val Glu Lys Thr Ser
            290                 295                 300 acc gaa gtc caa tgc aaa ggc ggg aat gtc tgc gtg caa gct cag gat    960
Thr Glu Val Gln Cys Lys Gly Gly Asn Val Cys Val Gln Ala Gln Asp
            305                 310                 315 cgc tat tac aat tcc tcr tgc agc aag tgg gca tgt gtt ccc tgc agg   1008
Arg Tyr Tyr Asn Ser Xaa Cys Ser Lys Trp Ala Cys Val Pro Cys Arg
320                 325                 330 gtc cga tcc tct aga ggt gga tca ggc tcc gga ggt agt gga ggt ggg   1056
Val Arg Ser Ser Arg Gly Gly Ser Gly Ser Gly Gly Ser Gly Gly Gly
335                 340                 345                 350 gga tct aag ctt ctg gct gtg cct agg agt agc agt cct gac tgg gct   1104
Gly Ser Lys Leu Leu Ala Val Pro Arg Ser Ser Ser Pro Asp Trp Ala
                355                 360                 365 cag tgc cag cag ctc tct cgg aat ctc tgc atg cta gcc tgg aac gca   1152
Gln Cys Gln Gln Leu Ser Arg Asn Leu Cys Met Leu Ala Trp Asn Ala
            370                 375                 380 cat gca cca gcg gga cat atg aat cta cta aga gaa gaa gag gat gaa   1200
His Ala Pro Ala Gly His Met Asn Leu Leu Arg Glu Glu Glu Asp Glu
            385                 390                 395 gag act aaa aat aat gtg ccc cgt atc cag tgt gaa gat ggt tgt gac   1248
Glu Thr Lys Asn Asn Val Pro Arg Ile Gln Cys Glu Asp Gly Cys Asp
400                 405                 410 cca caa gga ctc aag gac aac agc cag ttc tgc ttg caa agg atc cgc   1296
Pro Gln Gly Leu Lys Asp Asn Ser Gln Phe Cys Leu Gln Arg Ile Arg
415                 420                 425                 430 caa ggt ctg gtt ttt tat aag cac ctg ctt gac tct gac atc ttc aaa   1344
Gln Gly Leu Val Phe Tyr Lys His Leu Leu Asp Ser Asp Ile Phe Lys
                435                 440                 445 ggg gag cct gct cta ctc cct gat agc ccc atg gag caa ctt cac acc   1392
Gly Glu Pro Ala Leu Leu Pro Asp Ser Pro Met Glu Gln Leu His Thr
            450                 455                 460 tcc cta cta gga ctc agc caa ctc ctc cag cca gag gat cac ccc cgg   1440
Ser Leu Leu Gly Leu Ser Gln Leu Leu Gln Pro Glu Asp His Pro Arg
            465                 470                 475 gag acc caa cag atg ccc agc ctg agt tct agt cag cag tgg cag cgc   1488
```

```
                    Glu Thr Gln Gln Met Pro Ser Leu Ser Ser Gln Gln Trp Gln Arg
                        480                 485                 490 ccc ctt ctc cgt tcc aag atc ctt cga agc ctc cag gcc ttt ttg gcc        1536
Pro Leu Leu Arg Ser Lys Ile Leu Arg Ser Leu Gln Ala Phe Leu Ala
495                 500                 505                 510 ata gct gcc cgg gtc ttt gcc cac gga gca gca act ctg act gag ccc        1584
Ile Ala Ala Arg Val Phe Ala His Gly Ala Ala Thr Leu Thr Glu Pro
                515                 520                 525 tta gtg cca aca gct taagcggccg c                                       1610
Leu Val Pro Thr Ala
            530

<210> SEQ ID NO 6
<211> LENGTH: 531
<212> TYPE: PRT
<213> ORGANISM: Mus musculus
<220> FEATURE:
<221> NAME/KEY: misc_feature
<222> LOCATION: (85)..(85)
<223> OTHER INFORMATION: The 'Xaa' at location 85 stands for Leu.
<220> FEATURE:
<221> NAME/KEY: misc_feature
<222> LOCATION: (324)..(324)
<223> OTHER INFORMATION: The 'Xaa' at location 324 stands for Ser.

<400> SEQUENCE: 6

Met Ser Ala Leu Leu Ile Leu Ala Leu Val Gly Ala Ala Val Ala Asp
1               5                   10                  15

Tyr Lys Asp Asp Asp Asp Lys Leu Met Trp Glu Leu Glu Lys Asp Val
                20                  25                  30

Tyr Val Val Glu Val Asp Trp Thr Pro Asp Ala Pro Gly Glu Thr Val
            35                  40                  45

Asn Leu Thr Cys Asp Thr Pro Glu Glu Asp Asp Ile Thr Trp Thr Ser
    50                  55                  60

Asp Gln Arg His Gly Val Ile Gly Ser Gly Lys Thr Leu Thr Ile Thr
65                  70                  75                  80

Val Lys Glu Phe Xaa Asp Ala Gly Gln Tyr Thr Cys His Lys Gly Gly
                85                  90                  95

Glu Thr Leu Ser His Ser His Leu Leu Leu His Lys Lys Glu Asn Gly
            100                 105                 110

Ile Trp Ser Thr Glu Ile Leu Lys Asn Phe Lys Asn Lys Thr Phe Leu
        115                 120                 125

Lys Cys Glu Ala Pro Asn Tyr Ser Gly Arg Phe Thr Cys Ser Trp Leu
    130                 135                 140

Val Gln Arg Asn Met Asp Leu Lys Phe Asn Ile Lys Ser Ser Ser Ser
145                 150                 155                 160

Ser Pro Asp Ser Arg Ala Val Thr Cys Gly Met Ala Ser Leu Ser Ala
                165                 170                 175

Glu Lys Val Thr Leu Asp Gln Arg Asp Tyr Glu Lys Tyr Ser Val Ser
            180                 185                 190

Cys Gln Glu Asp Val Thr Cys Pro Thr Ala Glu Glu Thr Leu Pro Ile
        195                 200                 205

Glu Leu Ala Leu Glu Ala Arg Gln Gln Asn Lys Tyr Glu Asn Tyr Ser
    210                 215                 220

Thr Ser Phe Phe Ile Arg Asp Ile Ile Lys Pro Asp Pro Pro Lys Asn
225                 230                 235                 240

Leu Gln Met Lys Pro Leu Lys Asn Ser Gln Val Glu Val Ser Trp Glu
                245                 250                 255
```

```
Tyr Pro Asp Ser Trp Ser Thr Pro His Ser Tyr Phe Ser Leu Lys Phe
            260                 265                 270

Phe Val Arg Ile Gln Arg Lys Lys Glu Lys Met Lys Glu Thr Glu Glu
        275                 280                 285

Gly Cys Asn Gln Lys Gly Ala Phe Leu Val Glu Lys Thr Ser Thr Glu
    290                 295                 300

Val Gln Cys Lys Gly Gly Asn Val Cys Val Gln Ala Gln Asp Arg Tyr
305                 310                 315                 320

Tyr Asn Ser Xaa Cys Ser Lys Trp Ala Cys Val Pro Cys Arg Val Arg
            325                 330                 335

Ser Ser Arg Gly Gly Ser Gly Ser Gly Ser Gly Gly Gly Ser
            340                 345                 350

Lys Leu Leu Ala Val Pro Arg Ser Ser Pro Asp Trp Ala Gln Cys
        355                 360                 365

Gln Gln Leu Ser Arg Asn Leu Cys Met Leu Ala Trp Asn Ala His Ala
    370                 375                 380

Pro Ala Gly His Met Asn Leu Leu Arg Glu Glu Asp Glu Glu Thr
385                 390                 395                 400

Lys Asn Asn Val Pro Arg Ile Gln Cys Glu Asp Gly Cys Asp Pro Gln
            405                 410                 415

Gly Leu Lys Asp Asn Ser Gln Phe Cys Leu Gln Arg Ile Arg Gln Gly
        420                 425                 430

Leu Val Phe Tyr Lys His Leu Leu Asp Ser Asp Ile Phe Lys Gly Glu
            435                 440                 445

Pro Ala Leu Leu Pro Asp Ser Pro Met Glu Gln Leu His Thr Ser Leu
450                 455                 460

Leu Gly Leu Ser Gln Leu Leu Gln Pro Glu Asp His Pro Arg Glu Thr
465                 470                 475                 480

Gln Gln Met Pro Ser Leu Ser Ser Gln Gln Trp Gln Arg Pro Leu
            485                 490                 495

Leu Arg Ser Lys Ile Leu Arg Ser Leu Gln Ala Phe Leu Ala Ile Ala
        500                 505                 510

Ala Arg Val Phe Ala His Gly Ala Ala Thr Leu Thr Glu Pro Leu Val
            515                 520                 525

Pro Thr Ala
    530

<210> SEQ ID NO 7
<211> LENGTH: 1580
<212> TYPE: DNA
<213> ORGANISM: Homo sapiens
<220> FEATURE:
<221> NAME/KEY: CDS
<222> LOCATION: (7)..(1569)

<400> SEQUENCE: 7 agatct atg tct gca ctt ctg atc cta gct ctt gtt gga gct gca gtt         48
       Met Ser Ala Leu Leu Ile Leu Ala Leu Val Gly Ala Ala Val
         1               5                  10 gct gac tac aaa gac gat gac gac aag ctt ata tgg gaa ctg aag aaa        96
Ala Asp Tyr Lys Asp Asp Asp Asp Lys Leu Ile Trp Glu Leu Lys Lys
 15                  20                  25                  30 gat gtt tat gtc gta gaa ttg gat tgg tat ccg gat gcc cct gga gaa       144
Asp Val Tyr Val Val Glu Leu Asp Trp Tyr Pro Asp Ala Pro Gly Glu
                 35                  40                  45 atg gtg gtc ctc acc tgt gac acc cct gaa gaa gat ggt atc acc tgg       192
Met Val Val Leu Thr Cys Asp Thr Pro Glu Glu Asp Gly Ile Thr Trp
```

-continued

```
                   50                  55                  60
acc ttg gac cag agc agt gag gtc tta ggc tct ggc aaa acc ctg acc        240
Thr Leu Asp Gln Ser Ser Glu Val Leu Gly Ser Gly Lys Thr Leu Thr
            65                  70                  75 atc caa gtc aaa gag ttt gga gat gct ggc cag tac acc tgt cac aaa        288
Ile Gln Val Lys Glu Phe Gly Asp Ala Gly Gln Tyr Thr Cys His Lys
        80                  85                  90 gga ggc gag gtt cta agc cat tcg ctc ctg ctt ctt cac aaa aag gaa        336
Gly Gly Glu Val Leu Ser His Ser Leu Leu Leu Leu His Lys Lys Glu
 95                 100                 105                 110 gat gga att tgg tcc act gat att tta aag gac cag aaa gaa ccc aaa        384
Asp Gly Ile Trp Ser Thr Asp Ile Leu Lys Asp Gln Lys Glu Pro Lys
                115                 120                 125 aat aag acc ttt cta aga tgc gag gcc aag aat tat tct gga cgt ttc        432
Asn Lys Thr Phe Leu Arg Cys Glu Ala Lys Asn Tyr Ser Gly Arg Phe
            130                 135                 140 acc tgc tgg tgg ctg acg aca atc agt act gat ttg aca ttc agt gtc        480
Thr Cys Trp Trp Leu Thr Thr Ile Ser Thr Asp Leu Thr Phe Ser Val
        145                 150                 155 aaa agc agc aga ggc tct tct gac ccc caa ggg gtg acg tgc gga gct        528
Lys Ser Ser Arg Gly Ser Ser Asp Pro Gln Gly Val Thr Cys Gly Ala
    160                 165                 170 gct aca ctc tct gca gag aga gtc aga ggg gac aac aag gag tat gag        576
Ala Thr Leu Ser Ala Glu Arg Val Arg Gly Asp Asn Lys Glu Tyr Glu
175                 180                 185                 190 tac tca gtg gag tgc cag gag gac agt gcc tgc cca gct gct gag gag        624
Tyr Ser Val Glu Cys Gln Glu Asp Ser Ala Cys Pro Ala Ala Glu Glu
                195                 200                 205 agt ctg ccc att gag gtc atg gtg gat gcc gtt cac aag ctc aag tat        672
Ser Leu Pro Ile Glu Val Met Val Asp Ala Val His Lys Leu Lys Tyr
            210                 215                 220 gaa aac tac acc agc agc ttc ttc atc agg gac atc atc aaa cct gac        720
Glu Asn Tyr Thr Ser Ser Phe Phe Ile Arg Asp Ile Ile Lys Pro Asp
        225                 230                 235 cca ccc aac aac ttg cag ctg aag cca tta aag aat tct cgg cag gtg        768
Pro Pro Asn Asn Leu Gln Leu Lys Pro Leu Lys Asn Ser Arg Gln Val
    240                 245                 250 gag gtc agc tgg gag tac cct gac acc tgg agt act cca cat tcc tac        816
Glu Val Ser Trp Glu Tyr Pro Asp Thr Trp Ser Thr Pro His Ser Tyr
255                 260                 265                 270 ttc tcc ctg aca ttc tgc gtt cag gtc cag ggc aag agc aag aga gaa        864
Phe Ser Leu Thr Phe Cys Val Gln Val Gln Gly Lys Ser Lys Arg Glu
                275                 280                 285 aag aaa gat aga gtc ttc acc gac aag acc tca gcc acg gtc atc tgc        912
Lys Lys Asp Arg Val Phe Thr Asp Lys Thr Ser Ala Thr Val Ile Cys
            290                 295                 300 cgc aaa aat gcc agc att agc gtg cgg gcc cag gac cgc tac tat agc        960
Arg Lys Asn Ala Ser Ile Ser Val Arg Ala Gln Asp Arg Tyr Tyr Ser
        305                 310                 315 tca tct tgg agc gaa tgg gca tct gtg ccc tgc agt ggt agc ggc tct       1008
Ser Ser Trp Ser Glu Trp Ala Ser Val Pro Cys Ser Gly Ser Gly Ser
    320                 325                 330 tct aga ggt gga tca ggc tcc gga ggt agt gga ggt ggg gga tct aag       1056
Ser Arg Gly Gly Ser Gly Ser Gly Gly Ser Gly Gly Gly Gly Ser Lys
335                 340                 345                 350 ctt aga gct gtg cct ggg ggc agc agc cct gcc tgg act cag tgc cag       1104
Leu Arg Ala Val Pro Gly Gly Ser Ser Pro Ala Trp Thr Gln Cys Gln
                355                 360                 365 cag ctt tca cag aag ctc tgc aca ctg gcc tgg agt gca cat cca cta       1152
```

```
Gln Leu Ser Gln Lys Leu Cys Thr Leu Ala Trp Ser Ala His Pro Leu
            370                 375                 380 gtg gga cac atg gat cta aga gaa gag gga gat gaa gag act aca aat      1200
Val Gly His Met Asp Leu Arg Glu Glu Gly Asp Glu Glu Thr Thr Asn
        385                 390                 395 gat gtt ccc cat atc cag tgt gga gat ggc tgt gac ccc caa gga ctc      1248
Asp Val Pro His Ile Gln Cys Gly Asp Gly Cys Asp Pro Gln Gly Leu
    400                 405                 410 agg gac aac agt cag ttc tgc ttg caa agg atc cac cag ggt ctg att      1296
Arg Asp Asn Ser Gln Phe Cys Leu Gln Arg Ile His Gln Gly Leu Ile
415                 420                 425                 430 ttt tat gag aag ctg cta gga tcg gat att ttc aca ggg gag cct tct      1344
Phe Tyr Glu Lys Leu Leu Gly Ser Asp Ile Phe Thr Gly Glu Pro Ser
                435                 440                 445 ctg ctc cct gat agc cct gtg gcg cag ctt cat gcc tcc cta ctg ggc      1392
Leu Leu Pro Asp Ser Pro Val Ala Gln Leu His Ala Ser Leu Leu Gly
            450                 455                 460 ctc agc caa ctc ctg cag cct gag ggt cac cac tgg gag act cag cag      1440
Leu Ser Gln Leu Leu Gln Pro Glu Gly His His Trp Glu Thr Gln Gln
        465                 470                 475 att cca agc ctc agt ccc agc cag cca tgg cag cgt ctc ctt ctc cgc      1488
Ile Pro Ser Leu Ser Pro Ser Gln Pro Trp Gln Arg Leu Leu Leu Arg
    480                 485                 490 ttc aaa atc ctt cgc agc ctc cag gcc ttt gtg gct gta gcc gcc cgg      1536
Phe Lys Ile Leu Arg Ser Leu Gln Ala Phe Val Ala Val Ala Ala Arg
495                 500                 505                 510 gtc ttt gcc cat gga gca gca acc ctg agt ccc taagcggccg c             1580
Val Phe Ala His Gly Ala Ala Thr Leu Ser Pro
                515                 520

<210> SEQ ID NO 8
<211> LENGTH: 521
<212> TYPE: PRT
<213> ORGANISM: Homo sapiens

<400> SEQUENCE: 8

Met Ser Ala Leu Leu Ile Leu Ala Leu Val Gly Ala Ala Val Ala Asp
1               5                   10                  15

Tyr Lys Asp Asp Asp Lys Leu Ile Trp Glu Leu Lys Lys Asp Val
            20                  25                  30

Tyr Val Val Glu Leu Asp Trp Tyr Pro Asp Ala Pro Gly Glu Met Val
        35                  40                  45

Val Leu Thr Cys Asp Thr Pro Glu Glu Asp Gly Ile Thr Trp Thr Leu
    50                  55                  60

Asp Gln Ser Ser Glu Val Leu Gly Ser Gly Lys Thr Leu Thr Ile Gln
65                  70                  75                  80

Val Lys Glu Phe Gly Asp Ala Gly Gln Tyr Thr Cys His Lys Gly Gly
                85                  90                  95

Glu Val Leu Ser His Ser Leu Leu Leu Leu His Lys Lys Glu Asp Gly
            100                 105                 110

Ile Trp Ser Thr Asp Ile Leu Lys Asp Gln Lys Glu Pro Lys Asn Lys
        115                 120                 125

Thr Phe Leu Arg Cys Glu Ala Lys Asn Tyr Ser Gly Arg Phe Thr Cys
    130                 135                 140

Trp Trp Leu Thr Thr Ile Ser Thr Asp Leu Thr Phe Ser Val Lys Ser
145                 150                 155                 160

Ser Arg Gly Ser Ser Asp Pro Gln Gly Val Thr Cys Gly Ala Ala Thr
                165                 170                 175
```

Leu Ser Ala Glu Arg Val Arg Gly Asp Asn Lys Glu Tyr Glu Tyr Ser
            180                 185                 190

Val Glu Cys Gln Glu Asp Ser Ala Cys Pro Ala Ala Glu Glu Ser Leu
        195                 200                 205

Pro Ile Glu Val Met Val Asp Ala Val His Lys Leu Lys Tyr Glu Asn
    210                 215                 220

Tyr Thr Ser Ser Phe Phe Ile Arg Asp Ile Ile Lys Pro Asp Pro Pro
225                 230                 235                 240

Asn Asn Leu Gln Leu Lys Pro Leu Lys Asn Ser Arg Gln Val Glu Val
                245                 250                 255

Ser Trp Glu Tyr Pro Asp Thr Trp Ser Thr Pro His Ser Tyr Phe Ser
            260                 265                 270

Leu Thr Phe Cys Val Gln Val Gln Gly Lys Ser Lys Arg Glu Lys Lys
        275                 280                 285

Asp Arg Val Phe Thr Asp Lys Thr Ser Ala Thr Val Ile Cys Arg Lys
    290                 295                 300

Asn Ala Ser Ile Ser Val Arg Ala Gln Asp Arg Tyr Tyr Ser Ser Ser
305                 310                 315                 320

Trp Ser Glu Trp Ala Ser Val Pro Cys Ser Gly Ser Gly Ser Ser Arg
                325                 330                 335

Gly Gly Ser Gly Ser Gly Gly Ser Gly Gly Gly Ser Lys Leu Arg
            340                 345                 350

Ala Val Pro Gly Gly Ser Ser Pro Ala Trp Thr Gln Cys Gln Gln Leu
        355                 360                 365

Ser Gln Lys Leu Cys Thr Leu Ala Trp Ser Ala His Pro Leu Val Gly
    370                 375                 380

His Met Asp Leu Arg Glu Gly Asp Glu Glu Thr Thr Asn Asp Val
385                 390                 395                 400

Pro His Ile Gln Cys Gly Asp Gly Cys Asp Pro Gln Gly Leu Arg Asp
                405                 410                 415

Asn Ser Gln Phe Cys Leu Gln Arg Ile His Gln Gly Leu Ile Phe Tyr
            420                 425                 430

Glu Lys Leu Leu Gly Ser Asp Ile Phe Thr Gly Glu Pro Ser Leu Leu
        435                 440                 445

Pro Asp Ser Pro Val Ala Gln Leu His Ala Ser Leu Gly Leu Ser
    450                 455                 460

Gln Leu Leu Gln Pro Glu Gly His His Trp Glu Thr Gln Gln Ile Pro
465                 470                 475                 480

Ser Leu Ser Pro Ser Gln Pro Trp Gln Arg Leu Leu Arg Phe Lys
                485                 490                 495

Ile Leu Arg Ser Leu Gln Ala Phe Val Ala Val Ala Ala Arg Val Phe
            500                 505                 510

Ala His Gly Ala Ala Thr Leu Ser Pro
        515                 520

<210> SEQ ID NO 9
<211> LENGTH: 711
<212> TYPE: DNA
<213> ORGANISM: Mus musculus

<400> SEQUENCE: 9
atgaccatgc tctcactagc tcctctcctc agccttcttc tcctctgtgt ctctgattct    60
agggcagaaa caactgtgac ccagtctcca gcatccctgt ccgtggctac aggagaaaaa   120

-continued

```
gtcactatca gatgcataac cagcactgat attgatgatg atatgatctg gtaccagcag    180
aagccagggg aacctcctaa gctccttatt tcagaaggca atactcttcg tcctggagtc    240
ccatcccgct tctccagcag tggctatggc acagattttg tttttacaat tgaaaacacg    300
ctctcagaag atgttgcaga ttactactgt ttgcaaagtg ataacatgcc tctcacgttc    360
ggtgctggga ccaaggtgga gctgaaacgg gctgatgctg caccaactgt atccatcttc    420
ccaccatcca tggaacagtt aacatctgga ggtgccacag tcgtgtgctt cgtgaacaac    480
ttctatccca gagacatcag tgtcaagtgg aagattgatg gcagtgaaca acgagatggt    540
gtcctggaca gtgttactga tcaggacagc aaagacagca cgtacagcat gagcagcacc    600
ctctcgttga ccaaggttga atatgaaagg cataacctct atacctgtga ggttgttcat    660
aagacatcat cctcacccgt cgtcaagagc ttcaacagga atgagtgtta g             711
```

<210> SEQ ID NO 10
<211> LENGTH: 236
<212> TYPE: PRT
<213> ORGANISM: Mus musculus

<400> SEQUENCE: 10

```
Met Thr Met Leu Ser Leu Ala Pro Leu Leu Ser Leu Leu Leu Leu Cys
1               5                   10                  15

Val Ser Asp Ser Arg Ala Glu Thr Thr Val Thr Gln Ser Pro Ala Ser
            20                  25                  30

Leu Ser Val Ala Thr Gly Glu Lys Val Thr Ile Arg Cys Ile Thr Ser
        35                  40                  45

Thr Asp Ile Asp Asp Asp Met Ile Trp Tyr Gln Gln Lys Pro Gly Glu
    50                  55                  60

Pro Pro Lys Leu Leu Ile Ser Glu Gly Asn Thr Leu Arg Pro Gly Val
65                  70                  75                  80

Pro Ser Arg Phe Ser Ser Gly Tyr Gly Thr Asp Phe Val Phe Thr
                85                  90                  95

Ile Glu Asn Thr Leu Ser Glu Asp Val Ala Asp Tyr Tyr Cys Leu Gln
            100                 105                 110

Ser Asp Asn Met Pro Leu Thr Phe Gly Ala Gly Thr Lys Val Glu Leu
        115                 120                 125

Lys Arg Ala Asp Ala Ala Pro Thr Val Ser Ile Phe Pro Pro Ser Met
    130                 135                 140

Glu Gln Leu Thr Ser Gly Gly Ala Thr Val Val Cys Phe Val Asn Asn
145                 150                 155                 160

Phe Tyr Pro Arg Asp Ile Ser Val Lys Trp Lys Ile Asp Gly Ser Glu
                165                 170                 175

Gln Arg Asp Gly Val Leu Asp Ser Val Thr Asp Gln Asp Ser Lys Asp
            180                 185                 190

Ser Thr Tyr Ser Met Ser Ser Thr Leu Ser Leu Thr Lys Val Glu Tyr
        195                 200                 205

Glu Arg His Asn Leu Tyr Thr Cys Glu Val Val His Lys Thr Ser Ser
    210                 215                 220

Ser Pro Val Val Lys Ser Phe Asn Arg Asn Glu Cys
225                 230                 235
```

<210> SEQ ID NO 11
<211> LENGTH: 1406
<212> TYPE: DNA
<213> ORGANISM: Mus musculus -continued

```
<400> SEQUENCE: 11
atgggatgga gctgtatcat cctcttcttg gtagcaacag ctacaggtgt ccactcccag      60
gtccaactgc agcagcctgg ggctgagctg gtgaggcctg gggcttcagg gaagctgtcc     120
tgcaaggctt ctggctacac cttcaccagc tactggatga actgggtgaa gcagaggcct     180
ggacaaggcc ttgaatggat tggtatgatt gatcctttag acagtgaaac tcactataat     240
caaatgttca aggacaaggc cacattgact gtagacaaat cctccagcac agcctacatg     300
cagctcagca gcctgacatc tgaggactat gcggtctatt actgtgcaag aggggataac     360
tactatgcta tggactactg gggtcaagga acctcagtca ccgtctcctc agccaaaacg     420
acacccccat ctgtctatcc actggcccct ggatctgctg cccaaactaa ctccatggtg     480
accctgggat gcctggtcaa gggctatttc cctgagccag tgacagtgac ctggaactct     540
ggatccctgt ccagcggtgt gcacaccttc ccagctgtcc tgcagtctga cctctacact     600
ctgagcagct cagtgactgt cccctccagc acctggccca gcgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt ccccccaaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
cccatcatgc accaggactg gctcaatggc aaggagttca atgcagggt caacagtgca    1020 gctttccctg cccccatcga gaaaaccatc tccaaaacca aggcagacc gaaggctcca    1080 caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggact cagatggctc ttacttcgtc    1260
tacagcaagc tcaatgtgca gaagagcaac tgggaggcag gaaatacttt cacctgctct    1320
gtgttacatg agggcctgca caaccaccat actgagaaga gcctctccca ctctcctggt    1380
aaatgatccc agagtccagt ggcccc                                         1406
```

```
<210> SEQ ID NO 12
<211> LENGTH: 467
<212> TYPE: PRT
<213> ORGANISM: Mus musculus

<400> SEQUENCE: 12

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Gly Lys Leu Ser Cys Lys Ala Ser Gly Tyr Thr Phe
            35                  40                  45

Thr Ser Tyr Trp Met Asn Trp Val Lys Gln Arg Pro Gly Gln Gly Leu
        50                  55                  60

Glu Trp Ile Gly Met Ile Asp Pro Leu Asp Ser Glu Thr His Tyr Asn
65                  70                  75                  80

Gln Met Phe Lys Asp Lys Ala Thr Leu Thr Val Asp Lys Ser Ser Ser
                85                  90                  95

Thr Ala Tyr Met Gln Leu Ser Ser Leu Thr Ser Glu Asp Tyr Ala Val
                100                 105                 110
```

```
Tyr Tyr Cys Ala Arg Gly Asp Asn Tyr Tyr Ala Met Asp Tyr Trp Gly
        115                 120                 125

Gln Gly Thr Ser Val Thr Val Ser Ser Ala Lys Thr Thr Pro Pro Ser
        130                 135                 140

Val Tyr Pro Leu Ala Pro Gly Ser Ala Ala Gln Thr Asn Ser Met Val
145                     150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
            195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
            275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
            325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
            355                 360                 365

Lys Glu Gln Met Ala Lys Asp Lys Val Ser Leu Thr Cys Met Ile Thr
            370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Ser Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys Ser Gln Ser
    450                 455                 460

Pro Val Ala
465
```